US006246361B1

(12) United States Patent
Weill et al.

(10) Patent No.: US 6,246,361 B1
(45) Date of Patent: Jun. 12, 2001

(54) METHOD AND APPARATUS FOR DETERMINING A GEOGRAPHICAL LOCATION OF A MOBILE COMMUNICATION UNIT

(75) Inventors: Lawrence R. Weill, Seal Beach, CA (US); Gary Sutton, 1865 Caminito Ascua, La Jolla, CA (US) 92037

(73) Assignee: Gary Sutton, La Jolla, CA (US)

( * ) Notice: Subject to any disclaimer, the term of this patent is extended or adjusted under 35 U.S.C. 154(b) by 0 days.

(21) Appl. No.: 09/340,534

(22) Filed: Jun. 28, 1999

(51) Int. Cl.$^7$ .................................................. H04B 7/185
(52) U.S. Cl. ........................................................ 342/357.01
(58) Field of Search .............................. 342/357.01, 457, 342/352, 353, 357.03, 357.04, 357.1, 357.16; 701/213

(56) References Cited

U.S. PATENT DOCUMENTS

| 5,610,615 | 3/1997 | Chiodini . |
| 5,623,269 | 4/1997 | Hirshfield et al. . |
| 5,634,190 | 5/1997 | Wiedeman . |
| 5,678,175 | 10/1997 | Stuart et al. . |
| 5,729,205 | 3/1998 | Kwon . |
| 5,758,261 | 5/1998 | Wiedeman . |
| 6,072,430 | * 6/2000 | Wyrwas et al. ................... 342/357.1 |

FOREIGN PATENT DOCUMENTS

| 0 298 571 A1 | 1/1989 | (EP) . |
| 0 462 648 A2 | 12/1991 | (EP) . |
| 2 321 812 | 8/1998 | (GB) . |
| WO 98/01768 A1 | 1/1998 | (WO) . |

* cited by examiner

*Primary Examiner*—Daniel T. Pihulic
(74) *Attorney, Agent, or Firm*—Brown, Martin, Haller & McClain

(57) ABSTRACT

The location of a mobile unit is determined by evaluating the instantaneous distances between an apparatus traveling above the surface of the earth and the mobile unit. The instantaneous distances are determined by measuring the travel time of a plurality of signals and calculating the distance based on the speed of the signal. One of two possible location regions is identified as the region including the location of the mobile unit by observing the motion of the mobile unit resulting from the rotation of the Earth.

43 Claims, 13 Drawing Sheets

US 6,246,361 B1

METHOD AND APPARATUS FOR DETERMINING A GEOGRAPHICAL LOCATION OF A MOBILE COMMUNICATION UNIT

BACKGROUND OF THE INVENTION

1. Field of the Invention

The present invention relates in general to a method and apparatus for determining a geographical location of a mobile unit and more specifically to a method and apparatus for determining a geographical location of a mobile unit using an apparatus traveling above the surface of the Earth.

2. Description of the Related Art Communication systems and techniques for determining the location of a mobile unit are known. Many techniques utilize Global Positioning Systems (GPS) which allow a mobile unit to determine its position based on signals from at least three satellites. GPS systems work well when the mobile unit is in an open area such on an ocean or in the air. However, GPS systems are limited in that the mobile unit must have unobstructed paths to at least three GPS satellites. Some GPS systems require a minimum of four satellites to determine the location of a mobile unit. If substantially clear signals cannot be received from the required satellites by the mobile unit, the mobile unit cannot determine its position.

Techniques have been proposed that utilize Low Earth Orbit (LEO) satellite systems. Satellites in LEO systems orbit at a lower altitude than GPS satellites and are not geostationary but rather orbit the Earth at a high speed relative to GPS satellites. LEO satellite communication systems contain many more satellites than GPS systems in order to attain global coverage at a lower altitude.

At least one proposed technique for determining the position of a mobile unit, such as described in U.S. Pat. No. 5,610,615, attempts to take advantage of the LEO satellite's lower orbit and higher speed. This technique allows a mobile unit to determine its position by obtaining a signal from one satellite and determining an instantaneous elevation angle, angles related to the orbit track of the satellite and other parameters. However, this technique is disadvantaged in that calculations are complex requiring higher production and maintenance costs of the system. Further, the technique requires that the mobile unit process information and perform calculations, adding complexity, size and cost to mobile units. In addition to the disadvantages discussed above, the positioning method described in the references patent does not allow for an accuracy suitable for locating a mobile unit in emergency situations.

Systems requiring the mobile unit to determine its location are further disadvantaged in emergency situations. In emergency situations, a user may not be able to forward location information to emergency services. For example, a user may be losing consciousness or have limited communication abilities due to physical trauma experienced in an accident.

Therefore, there exists a need for a method and apparatus for simply and efficiently locating a mobile user and communicating the location to emergency service providers in times of emergency.

SUMMARY OF THE INVENTION

The present invention relates to a method and apparatus for locating a mobile unit using an apparatus traveling above the surface of the Earth by observing the travel times for signals transmitted between the mobile unit and the apparatus.

In several embodiments of the invention, travel times of signals transmitted between the mobile unit and a single satellite orbiting the Earth are used to determine instantaneous distances between the satellite and the mobile unit. Each of the instantaneous distances can be represented with a circle having the satellite as the center at a specific time. The intersection of any two circles results in two possible locations of the mobile unit. One of the two possible locations is identified as the location of the mobile unit by observing a movement of the mobile unit due to the rotation of the Earth.

In one embodiment of the invention, several signal pulses are transmitted from the satellite to the mobile unit. The mobile unit retransmits the signal pulses to the satellite after a predetermined retransmission delay. The satellite measures the elapsed time between the transmission of the signals from the satellite and the reception of the signals at the satellite. The instantaneous distance is calculated by subtracting the known retransmission delay from the elapsed time and dividing the result by twice the speed of the signal.

In another embodiment, the signals originate from a terrestrial station, are relayed by the satellite to the mobile unit and are re-transmitted to the terrestrial station through the satellite. The signal travel times between the satellite and the mobile unit are determined by subtracting the retransmission delays in the satellite and the mobile unit and subtracting signal travel times between the terrestrial station and the satellite.

In another embodiment of the invention, a terrestrial station determines the location of a mobile unit based on information forwarded by a single satellite orbiting the Earth including times of reception of signals transmitted from the mobile unit. The terrestrial station calculates the location of the mobile unit using the velocity (speed and direction) of the satellite, the location of the satellite, the difference between times of reception of the signal transmitted by the mobile, and the Earth's rotation.

In another embodiment of the invention, signals are transmitted from the mobile unit at times separated by predetermined time intervals. The instantaneous distances are determined by observing the reception times of the signals at the satellite.

BRIEF DESCRIPTION OF THE DRAWINGS

The present invention will be better understood from the following detailed description of a preferred embodiment of the invention, taken in conjunction with the accompanying drawings in which like reference numerals refer to parts and in which.

DESCRIPTION OF THE PREFERRED EMBODIMENT

Figure 1:
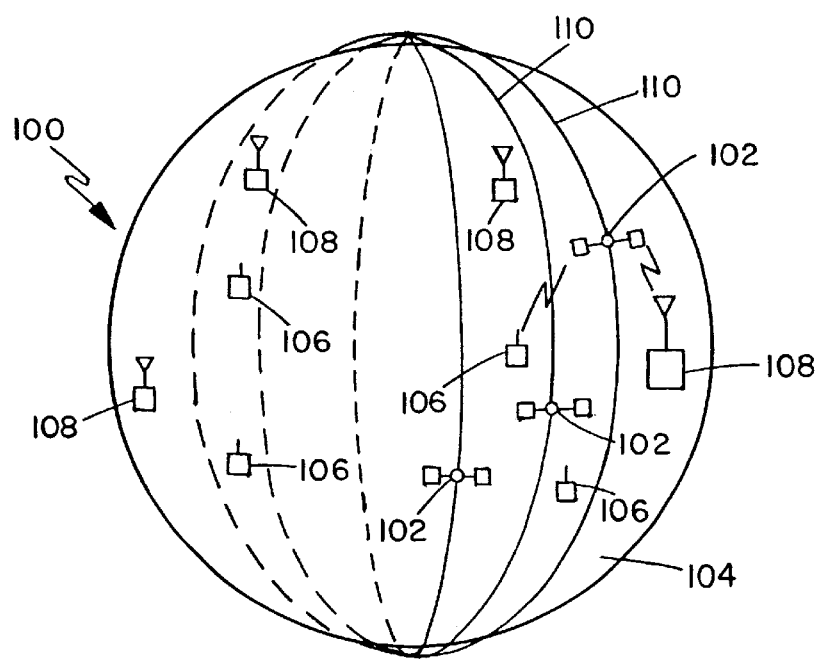
FIG. 1 is a block diagram satellite communication system in accordance with a preferred embodiment of the present invention.

FIG. 1 is block diagram of a satellite communication system 100 in accordance with a preferred embodiment of the present invention. The communication system 100, preferably, includes several Low Earth Orbit (LEO) satellites 102 orbiting the Earth 104, several mobile communication units 106, and several terrestrial stations 108. Several such systems are being implemented including the Iridium, Globalstar, Skybridge, and Teledesic systems. Depending on the particular communication system 100, the satellites 102 orbit the Earth at an altitude between 400 and 1000 miles above the Earth's surface. As is known, LEO satellites 102 travel in predefined orbit paths 110. LEO communication systems utilizing different technologies for communication. For example the Globalstar system uses Code Division Multiple Access (CDMA) techniques for communication. As will be apparent to those skilled in the art, the embodiments of the invention described herein may be implemented within any one of the several operating or proposed LEO satellite systems.

Mobile units 106 may be located anywhere on the surface (or near the surface) of the Earth 104 including locations on water such as rivers, oceans, lakes and other bodies of water. Further, depending on the terrain of the geographical region, the mobile unit 106 may be located at any elevation with respect to sea level.

As will be readily apparent to those skilled in the art, the present invention may be used in any communication system 100 utilizing an apparatus (102) traveling above the surface of the Earth 104 such as a satellite or an aircraft and is not limited to the particular embodiment described herein. For example, the apparatus may be located in a AWAC aircraft traveling in a defined path above the Earth 104. Accordingly, although the following description refers to a satellite 102 operating within a satellite communication system 100, the principles will apply to any apparatus (102) traveling above the surface of the Earth 104.

Figure 2:
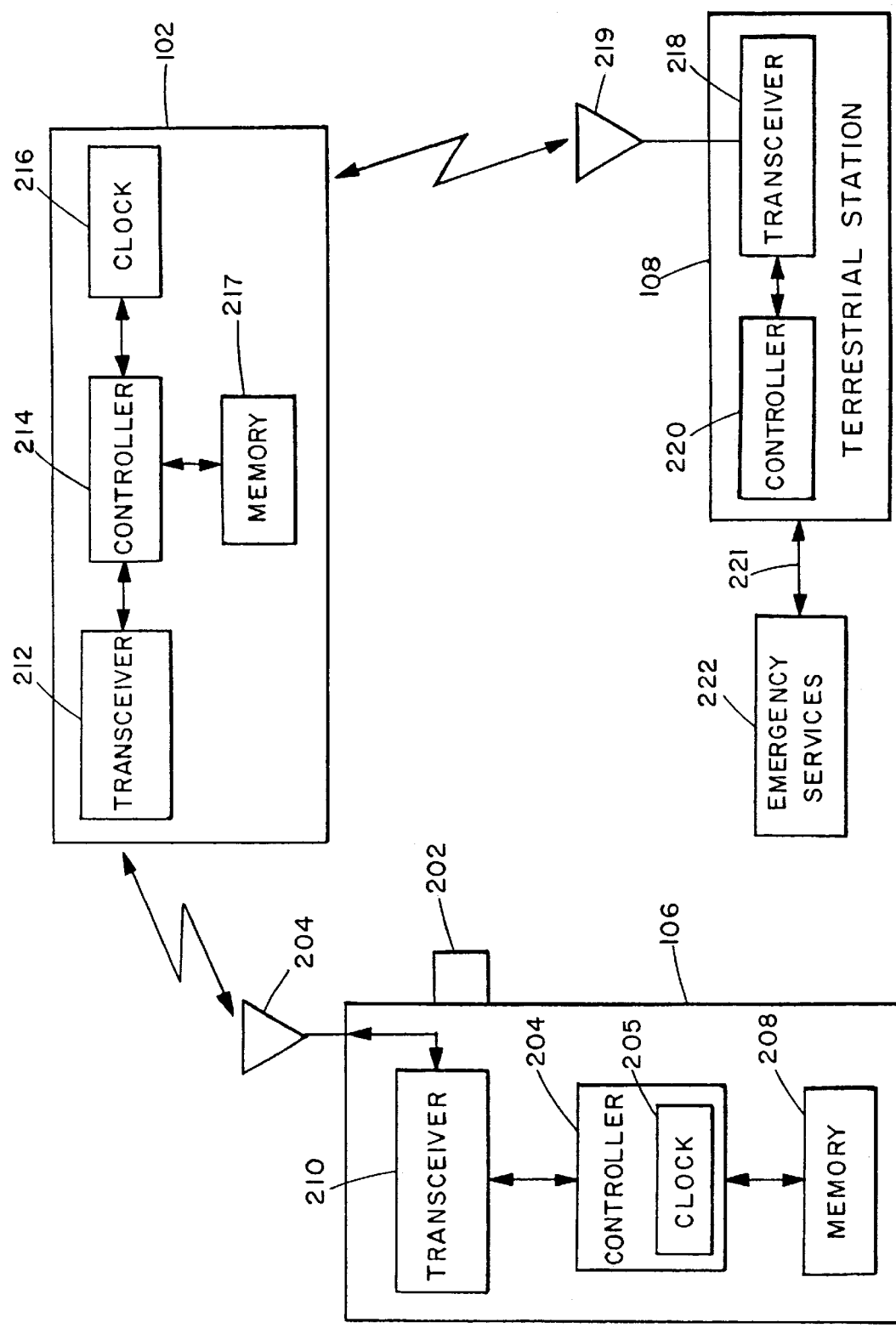
FIG. 2 is a block diagram of a portion of the communication system 100 in accordance with the preferred embodiment of the invention.

FIG. 2 is a block diagram of portion of the satellite communication system 100 in accordance with the preferred embodiment of the invention. The mobile unit 106 is constructed in accordance with the particular communication system 100 and is, preferably, used for voice and data communications as well as other communication services available through the communication system 100.

The mobile unit 106 includes a controller 204, a memory device 208, and a transceiver 210. The transceiver 210 includes a transmitter and a receiver capable of communicating within the satellite communication system 100 and is designed using known techniques. The transmitter includes a modulator for modulating signals in accordance with the protocol of the communication system and the receiver includes a demodulator for demodulating signals received at the receiver. As will be readily apparent to those skilled in the art, the circuitry required for the various receiver and transmitter functions may be implemented as a single circuit where appropriate in order to avoid redundancy, size and cost.

The memory device 208 is, preferably, an integrated circuit capable of storing information and can be any one of various types of memory devices. The controller 204 is a digital processor, micro-processor or any other type of processor capable of storing and running predetermined programs to facilitate the overall functionality of the mobile unit 106. In the preferred embodiment, the controller 204 includes a clock 205 such as a quartz crystal implemented with appropriate circuitry to provide a clock signal.

In an emergency situation (or any other time when the user wishes to determine the location of the mobile unit 106), the user of the mobile unit 106 initiates a location sequence by activating a switch 202. Preferably, the switch 202 is a push button switch that is quickly and easily accessible in times of emergency. Alternate methods to initiate the location sequence, however, may be used. For example, if the mobile unit 106 has voice recognition capabilities, the location sequence may be initiated by distinctive words uttered by the user such as "HELP". In other embodiments, the location sequence may be initiated by an "Officer Down" condition such as when the mobile unit 106 is in a horizontal rather than vertical (upright) position. Further, if the mobile unit 106 is integrated within a vehicle's safety system, the location sequence may be triggered by the activation of safety mechanism. For example, the location sequence by be initiated by the deployment of a vehicle safety airbag.

When the location initiation sequence is initiated, the controller 204 obtains a user identification number from memory 208 and sends the appropriate command signals to the transceiver 210 to transmit an activation signal through the antenna 209 to the satellite 102. In the preferred embodiment, the modulator within the transmitter modulates a radio frequency (RF) carrier in accordance with the protocol of the satellite communication system 100.

The satellite 102 includes a transceiver 212, a controller 214, a clock 216 and a memory device 217. The transceiver 212 includes a transmitter and a receiver capable of communicating within the satellite communication system 100. The transmitter includes a modulator for modulating signals in accordance with the protocol of the communication system 100 and the receiver includes a demodulator for demodulating signals received at the receiver either from the mobile unit 106 or the terrestrial station 108. The circuitry required for the various receiver and transmitter functions may be implemented as a single circuit where appropriate in order to avoid redundancy, size and cost.

The memory device 217 is, preferably, an integrated circuit capable of storing information and can be any one of various types of memory devices. The controller 214 is a digital processor, micro-processor or any other type of processor capable of storing and running predetermined programs to facilitate the overall functionality of the satellite 102. In the preferred embodiment, the satellite 102 includes a clock 216 such as quartz crystal oscillator implemented with appropriate circuitry to provide an accurate clock signal. Preferably, the clock 216 should have an accuracy of no less than ten parts per million. Many satellite systems, however, may require more accurate clocks within the satellite for applications beyond the present invention.

The activation signal is received by a receiver in the transceiver 212, demodulated, and forwarded to the controller 214. In the preferred embodiment, the controller 214 transmits a plurality of signals to the mobile unit 106 through the transceiver 212 at transmission times dictated by predetermined programs residing in the controller 214. The time between transmission times may range from approximately a few hundred milliseconds to several seconds and depends on several factors. The optimum timing of the transmission times depends on the particular satellite communication system 100 and parameters such as maximum time allowed for determining the location of the mobile unit, the desired accuracy of the estimated location, the speed of the satellite, the strength of the signals, the accuracy of the clocks (295, 216), the mobile unit retransmission delay, the maximum anticipated distance traveled by the signals and other factors recognized by those skilled in the art.

Each of the signals transmitted by the satellite 102 requires a finite signal travel time to reach the mobile unit 106. Because the satellite 102 is orbiting the Earth 104 and traveling with a velocity in relation to the mobile unit 106, the signals are not received at the predetermined period at which they were transmitted. In other words, if the signal pulses (signals) are transmitted at a period of once per second, the signals received at the satellite may be received at a period slightly less or slightly greater than a second depending on the relative motion between the satellite 102 and the mobile unit 106.

Although in the preferred embodiment the signals are described as pulses at a carrier frequency, those skilled in the art will recognize that other types of signals may be used such as pseudo random signals. In the case of continuous wave signals, the time measurements can be interpreted as phase measurements. Signals using pseudo-random codes allow for more signal energy to be transmitted and may result in more accurate distance measurements than pulse signals. In the interest of brevity and clarity, the principles described herein assume that the signals are pulses. However, those skilled in the art will recognize that the principles are easily applied to schemes utilizing other types of signals. One scheme using such codes requires the satellite 102 (or terrestrial station 108) to continuously transmit a ranging code which is tracked by the mobile unit 106 and continuously re-transmitted on a different frequency (to prevent interference with the incoming code). In an other scheme, the satellite 102 transmits the code signal periodically and receives the re-transmitted code in the intervening "quiet" periods. This second approach makes it unnecessary for either the mobile unit 106 or the satellite 102 to be receiving and transmitting simultaneously.

After the signals are received at the mobile unit 106, the mobile unit 106 transmits the signals back to the satellite 102 after a known retransmission delay. The retransmission delay is, preferably, measured by the controller 204 using the clock 205 and is approximately 50–200 microseconds. The mobile unit 106 is implemented in way that results in a minimal retransmission delay to minimize timing errors due to clock frequency error. The signals are received at the satellite 102 after a signal travel time. In the preferred embodiment, the signal travel time of each signal from the satellite 102 to the mobile unit 106 is approximately equal to the signal travel time for the same signal transmitted from the satellite 102 to the mobile unit 106 since the position of the satellite 102 does not significantly change during the round-trip travel time of the signal. The signal travel time of each signal is different compared to the signal travel time of other signals since the satellite 102 has an opportunity to move either toward or away from the mobile unit 106 during the time between signal transmission times.

As discussed below in detail, an instantaneous distance between the mobile unit 106 and the satellite 102 is determined for each signal based on the total elapsed time from the initial transmission of the signal from the satellite 102 to the reception of the signal at the satellite 102. Preferably, the satellite 102 "time stamps" each of the plurality of signals when it is received from the mobile unit 106. In other words, the reception times of each of the signals is recorded. Preferably, each recorded reception time is transmitted to the terrestrial station 108 in a message. The reception times may be transmitted to the terrestrial station 108 using any one of a variety of techniques. For example, several transmission and reception times may be stored and transmitted in a single message or a separate message can be sent corresponding to a single signal reception time or transmission time. Preferably, the satellite 102 stores the transmission and reception times for signals transmitted during a five to ten second interval before transmission to the terrestrial station 108. This allows the terrestrial station 108 to calculate the location of the mobile unit 106 in "real time" while minimizing the overhead associated with sending the reception and transmission times more frequently.

In the preferred embodiment, the terrestrial station 108 determines the location of the mobile unit 106 using the reception and transmission timing information determined by the satellite 102. The terrestrial station 108 receives the messages from the satellite 102 through an antenna 217 at a transceiver 218. The transceiver 218 includes a transmitter and a receiver capable of communicating within the satellite communication system 100. The transmitter includes a modulator for modulating signals in accordance with the protocol of the communication system 100 and the receiver includes a demodulator for demodulating signals received at the receiver from the satellite 102.

The messages received and demodulated by the transceiver 218 are sent to the controller 220. The controller 220 is a digital processor, micro-processor or any other type of processor capable of storing and running predetermined programs to facilitate the overall functionality of the terrestrial station 108. The controller 220 calculates two possible locations of the mobile unit 106 based on an intersection between two instantaneous distances. As will be discussed below, the instantaneous distances can be depicted as geometrical representations of a plurality of possible mobile unit 106 locations. In the preferred embodiment the geometric representations are circular while the geometric representations are hyperbolic in other embodiments. The position calculation results in two possible locations because the mobile unit 106 may be on one of either of two sides of the satellite orbit path 110. By observing the movement of the mobile unit 106 due to the rotation of the Earth 104, the terrestrial station 108 identifies one of the two locations as the location of the mobile unit 106. The controller 220 accesses a communication channel 221 such as public switched telephone network (PSTN) to forward the location information to emergency services 222. Any other type of communication channel or network may used to communicate the location of the mobile unit 106 to the emergency services 222. The communication network may be a cellular, microwave, radio frequency (RF) or any other type of wireless or wired communication network.

As will be discussed below, a plurality of instantaneous distances are determined and used to calculate the location of the mobile unit 106 in the preferred embodiment. The number of distance measurements that must be obtained to achieve a desired level of accuracy depends on the particular satellite communication system 100 and will approach a minimum of three measurements where two are required to determine the two possible locations and the third measurement is used to identify one of the two possible locations as the location of the mobile unit 106.

In a first alternate embodiment, the satellite (apparatus) 102 performs the function of a repeater station by relaying the plurality of signals directly from the terrestrial station 108 to the mobile unit 106 and relaying the re-transmitted signals from the mobile unit 106 to the terrestrial station 108. The terrestrial station 108 compensates for the communication delays using known techniques by subtracting the signal travel times between the satellite 102 and the terrestrial station 108 and other communication delays. In systems (100) utilizing packet switching schemes or other communication techniques that result in variable delays, additional computations using known techniques are necessary since the controller 220 must compensate for the variable delays. In the first alternate embodiment, therefore, the terrestrial station 108 determines the satellite 102 reception times based on the times that the plurality of signals are received at the terrestrial station 108 and other communication system 100 parameters.

In a second alternate embodiment, the satellite (apparatus) 102 determines the location of the mobile unit 106. The implementation of the second alternate embodiment is similar to the preferred embodiment except that calculations performed to determine the location of the mobile unit 106 are performed in the controller 214 of the satellite 102 rather than the controller of the terrestrial station 108. Accordingly, the location of the mobile unit 106 is transmitted to the terrestrial station 108 from the satellite 102 rather than the message containing the transmission and reception times.

As will be apparent to those skilled in the art, the method of determining the location of the mobile unit 106 may be performed in variety of hardware implementations without deviating from the intended scope of the invention. Calculations and determination of the location of the mobile unit 106 may be performed in a variety of system 100 locations. As explained above, the signals may be transmitted and received from the terrestrial station 218 through the satellite 102. Also, the calculations may be performed in the satellite 102 rather than the terrestrial station 108. Calculations may be partially performed in the satellite 102 and forwarded to the terrestrial station 108 for completion. Therefore, the following description of the method and calculations may be performed in the satellite 102, the terrestrial station 108, or any other device adequately coupled to the satellite 102 through a communication channel.

Figure 3A:
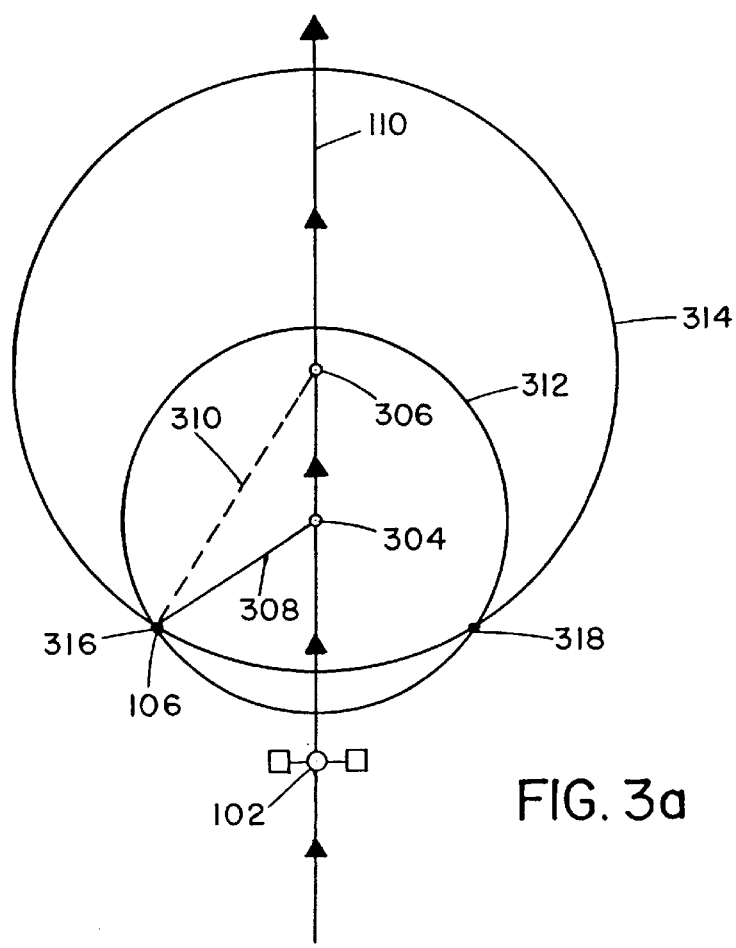
FIG. 3a is a top view of the apparatus traveling above the surface of the earth as the apparatus receives the first three signals of a plurality of signals from the mobile unit in accordance with the preferred embodiment.
Figure 3B:
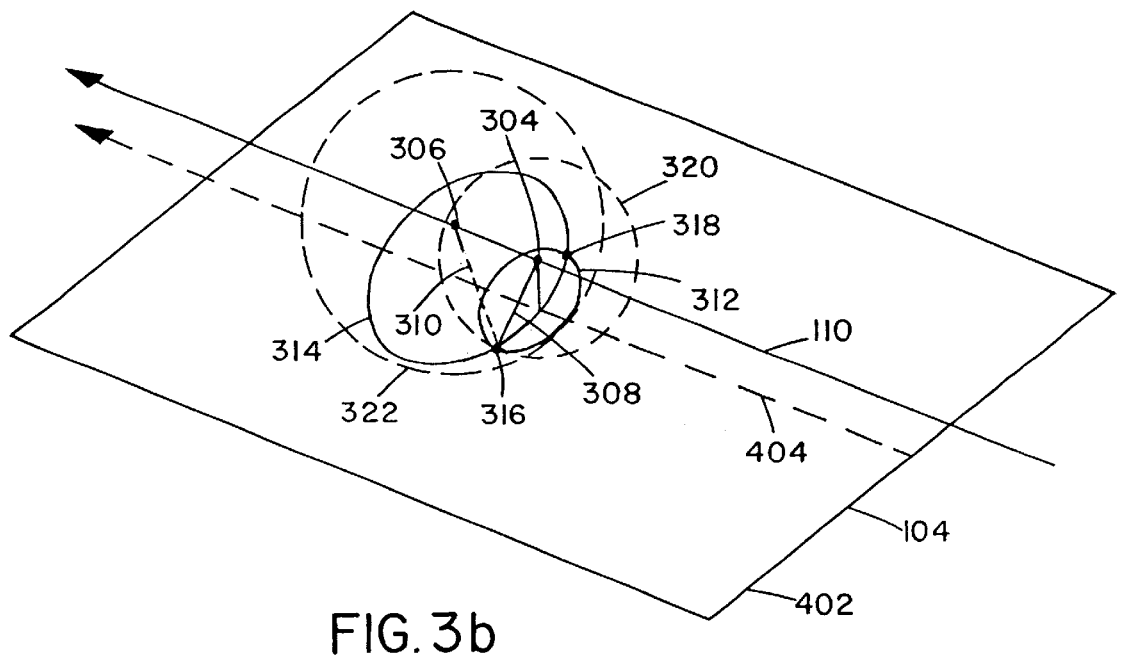
FIG. 3b is an isometric view of the apparatus traveling above the surface of the earth depicting the relationship between the instantaneous distances and the surface of the earth in accordance with the preferred embodiment of the invention.
Figure 3C:
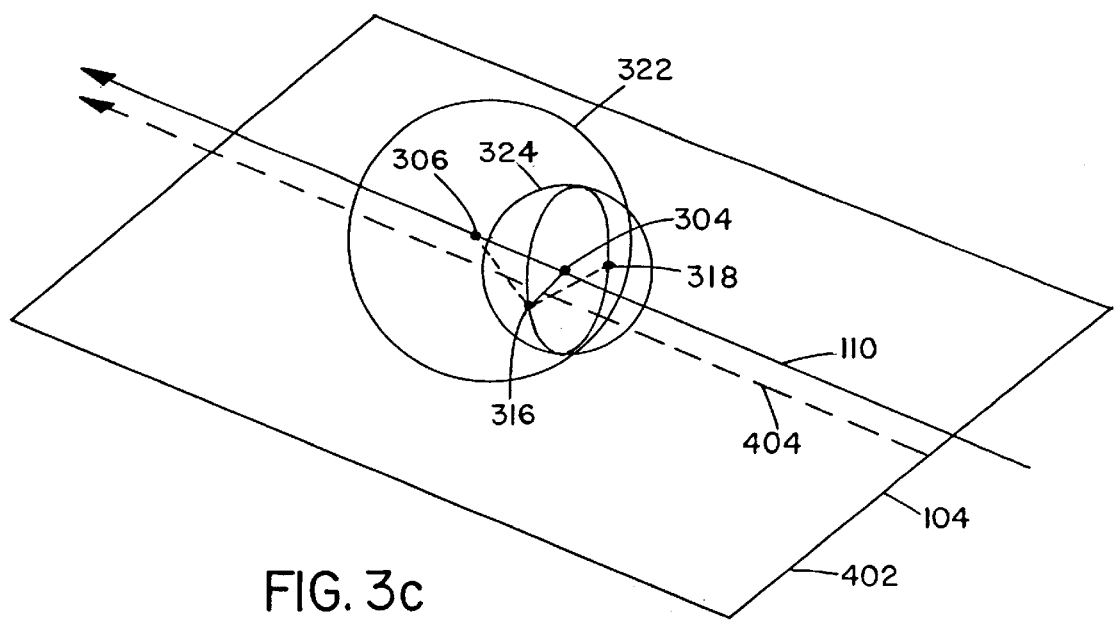
FIG. 3c is an isometric view of the apparatus traveling above the surface of the earth depicting the intersection between the first sphere and the second sphere in accordance with the preferred embodiment of the invention.

FIGS. 3a, 3b, 3c and 3d are simplified representations of a satellite (apparatus) 102 traveling above the surface of the earth 104 in accordance with the preferred embodiment of the invention. In order to avoid confusion, the representations in FIGS. 3a, 3b, 3c and 3d do not show the effects of the earth's 104 rotation on the mobile unit 106. FIGS. 3b and 3c are isometric representations of the satellite traveling above the surface of the earth 104 that is represented by a plane. The earth's 104 surface is represented by a plane for demonstrative purposes and those skilled in the art will recognize that the surface of the earth will more accurately be defined by a terrain function of the surface that may contain several different elevations.

FIG. 3a is a simplified representation of a top view of a satellite (apparatus) 102 orbiting the earth 104 in accordance with the preferred embodiment of the invention. As will be discussed below in more detail, the information regarding the terrain below the satellite is accessible by the satellite 102 and, therefore, the elevation of the mobile unit 106 is a known function of its lateral position. Accordingly, in order to minimize the complexity of the current illustration, FIG. 3a does not represent an elevation of the mobile unit 106 since the intersection of the lateral position and the function of the terrain yields the mobile unit's location. The intersection between the lateral position and the function of the terrain is discussed below in regard to FIGS. 3b, 3c and 3d.

Referring now to FIG. 3a, the satellite 102 transmits and receives the plurality of signals as it travels along the orbit path 110. The first signal is transmitted and received by the satellite 102 at a first signal reception time that corresponds to a first reception point 304 along the orbit path 110. The second signal is transmitted and received by the satellite 102 at a second signal reception time that corresponds to a second reception point 306. Since the elapsed time required for the round-trip of a signal is short relative to the time between the transmission times of the signals, the position of the satellite 102 during each of the reception times coincides with the position (304, 306) of the satellite 102 during each of the respective transmission times (304, 306) of the signals in FIG. 3a.

Although in the preferred embodiment a plurality of signals are transmitted and received by the satellite 102, FIG. 3 depicts two instantaneous distances for purposes of illustration. As mentioned above, the number of signals needed to determine the location of the mobile unit 106 approaches a minimum of three measurements: two measurements to determine two possible locations of the mobile unit 106 and a third to resolve the lateral ambiguity. In the preferred embodiment, the terrestrial station 108 determines a first instantaneous distance by measuring a first elapsed time from the first signal transmission time to the first signal reception time. The terrestrial station 108 subtracts the mobile unit re-transmission delay from the first elapsed time. The resulting value is approximately twice the first signal travel time. The first instantaneous distance between the satellite 102 and the mobile unit 106 is calculated by dividing the first signal travel time by the speed of the signal. Since the signals are electromagnetic signals in the preferred embodiment, the speed of the signal is chosen to be the speed of light (3×108 meters per second).

The second instantaneous distance is determined by dividing the second signal travel time by the speed of the second signal, where the second signal travel time is approximately half of the time resulting from a second elapsed time between the second signal transmission and the second signal reception time minus the mobile unit re-transmission delay.

As will be discussed below in reference to FIG. 3b, each of the instantaneous distances corresponds to an intersection between a sphere representing a plurality of possible locations of the mobile unit 106 at the corresponding transmission time and the surface of the earth 104. For purposes of FIG. 3a, however, the discussion is directed to a two dimensional coordinate system.

As shown in FIG. 3a, from the perspective of the apparatus 102, the first instantaneous distance is represented a first circle 312 having a center at the first reception point 304 and a radius (308) equal to the first instantaneous distance. The second instantaneous distance is represented by a second circle 314 having a center at the second reception point 306 and a radius (310) equal to the second instantaneous distance. Two possible locations (316, 318) of the mobile unit 106 are calculated based on the intersection of the first instantaneous distance and the second instantaneous distance. Therefore, the intersection of the first circle 312 and the second circle 314 results in two points (316, 318) which are symmetrically positioned with respect to the orbit path 110. As described below, the location of the mobile unit 106 is identified from the two points (316, 318) by observing the motion of the mobile unit 106 due to the rotation of the earth 104. Since FIG. 3a is a two-dimensional representation of the apparatus traveling over the earth, the centers 304, 306 are coincident with the locations of the apparatus at the reception times. However, as will be seen below in regard to FIG. 3b, the apparatus is not in the same plane as the circles and, therefore, the centers of the circles are the tips of two cones and the radii 308, 310 are sides of those cones where the circles 312, 314 are the bases of the cones, respectively.

FIG. 3b is an isometric representation of the satellite traveling above the surface of the earth 104. Although the earth's 104 surface below the satellite 102 will likely have variations in elevation, the surface of the earth 104 is represented by a flat plane 402 in FIG. 3b to minimize the complexity of the drawing and explanation. In the preferred embodiment, the information relating to the terrain is represented and stored as a plurality of equations. The satellite ground track 404 is directly below the satellite orbit path 110 and is represented by a dashed line in FIG. 3b. The plurality of possible mobile unit 106 locations at the first reception point 304 is represented by first sphere 320 and the plurality of possible mobile unit 106 locations at the second reception point 306 is represented by a second sphere 322. The intersection of the first and second spheres 320, 322 with the plane 402 results in the first and second circles 312 and 314 respectively. The first and second circles 312, 314 lie in the plane 402.

As shown in FIG. 3b, the first instantaneous distance and the second instantaneous distance do not lie in the plane 402. The two distances are extend diagonally from the first and second reception points 304, 306 respectfully to the location 316 of the mobile unit which does lie in the plane 402.

FIG. 3c is a second isometric representation of the apparatus 102 traveling above the surface of the earth 104 in accordance with the preferred embodiment that depicts the intersection of the first and second spheres 320, 322. The intersection of the first sphere 320 with the second sphere 322 results in a circle 324 that is perpendicular to the satellite orbit path 110. The circle 324 intersects the plane 402 at the two possible locations 316, 318 of the mobile unit 106. Therefore, as those skilled in the art will recognize, the two possible locations 316, 318 may be determined with various methods in accordance with the teachings herein. For example, the intersection of the first sphere and the second sphere can be calculated resulting a in a circle 324 of possible locations. The intersection of the circle 324 and the plane 404 (earth's surface 104) yields the two possible locations 316, 318 of the mobile unit 106. The two locations 316, 318 may also be calculated by determining the intersection between two circles 312, 314 located in the plane 402 where the two circles 312, 314 define the plurality of possible locations at the instantaneous distances lying within the plane 404.

Figure 3D:
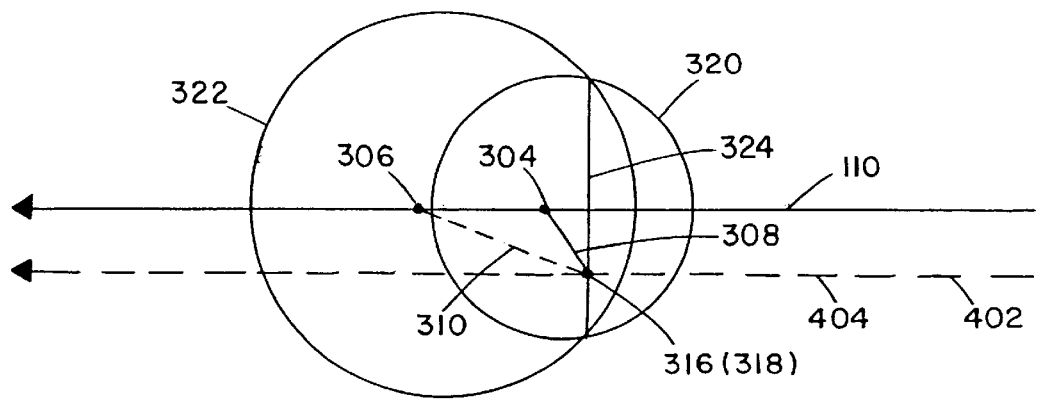
FIG. 3d is a side view of the apparatus traveling above the surface of the earth in accordance with the preferred embodiment of the invention.

FIG. 3d is a side view representation of the apparatus traveling above the surface of the earth 104 in accordance with the preferred embodiment of the invention. From this perspective, the circle 324 defining the intersection between the two spheres 320, 322 appears as a line (324) and the two possible locations 316, 318 appear to be coincident.

Figure 4:
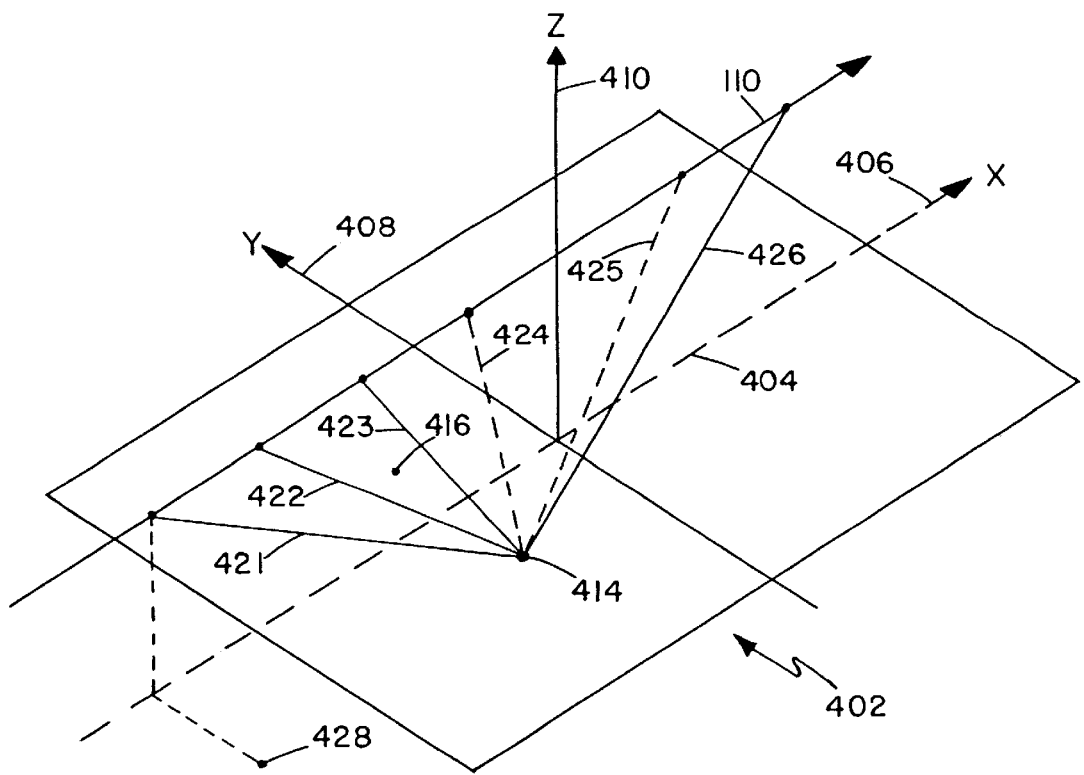
FIG. 4 is an isometric timing diagram of the apparatus traveling above the surface of the earth.

FIG. 4 is an isometric representation of an apparatus (satellite) 102 at a plurality of reception positions as it travels above the surface of the earth 104 in accordance with the preferred embodiment of the invention. As mentioned above, a plurality of instantaneous distance measurements $r_i$ 421–426 (308, 310) are calculated to determine the location of the mobile unit 106. The following description of the preferred method of calculating the location of the mobile unit 106 is, preferably, performed by the terrestrial station 108 receiving messages containing the transmission and reception times of the plurality of signals. The method may be performed in any one of the embodiments discussed by compensating for delays using known techniques. For example, and as reflected in the equations below, if the signals are transmitted and received by the terrestrial station 108, the signal delays due to the satellite 102, the retransmission delay in the mobile unit 106, and the travel times resulting from the signals traveling between the terrestrial station 108 and the satellite 102 can be subtracted from the total signal travel time for each transmitted signal.

In the preferred embodiment, the location of the mobile unit is determined by an iterative estimation technique using Newton's Method. The coordinate system chosen for this purpose is arbitrary, but for purposes of visualization it is convenient to consider a 3-dimensional Cartesian coordinate system with the x-y plane 402 tangent to the surface of an ellipsoidal model of the earth (such as WGS-84) at a point on the ground track 404 of the satellite and with the x axis 406, y axis 408, and z axis 410 as shown in FIG. 4.

Because the portion of the orbit path 110 which the satellite 102 traverses during instantaneous distance measurements will reasonably approximate a straight line parallel to the earth's 104 surface, the information contained in distance measurements to the satellite 102 can only determine the mobile unit 106 to be somewhere on a circle (312, 314) of known radius having a plane perpendicular to the orbital path 110. However, if the altitude coordinate z of the mobile unit is a known function z(x,y) of x and y, a surface is defined upon which the mobile unit 106 is located, and the intersection of this surface with the aforementioned circle (312, 314) yields two possible mobile unit locations (316, 318), 414, 416. The correct position can be determined by a technique to be described subsequently. The function z(x,y) can be stored at the terrestrial station 108 as a digital topographic map of the area in which the mobile unit 106 is located. Because the z component is a function of x and y, the position of the mobile unit 106 in 3-dimensional space is completely specified by the two-dimensional coordinate vector (x,y). The algorithm to be described finds the mobile unit 106 position which minimizes the least-squares objective function $$J(x, y) = \sum_{i=1}^{n} [r_i - d_i(x, y)]^2, \qquad (1)$$

where n is the number of instantaneous distance measurements, (x,y) is the mobile unit 106 position using the aforementioned coordinate system, $d_i(x,y)$ is the $i^{th}$ distance to the satellite 102 that would exist if the mobile unit 106 were at position (x,y) and $r_i$ is the $i^{th}$ instantaneous distance measurement 421–426 (including measurement noise) for the actual (but unknown) mobile unit location 414. The plurality of instantaneous distance measurements $r_i$ include $r_1$ 421, $r_2$ 422, $r_3$ 423, $r_4$ 424, $r_{n-1}$ 425, and $r_n$ 426. By minimizing J(x,y), the mobile unit position is obtained that gives the best match in obtained, in the least-squares sense, between the measured distances and the distances that should be observed.

A condition necessary to minimize J(x,y) is that $$J_x(x,y)=0 \qquad (2)$$

$$J_y(x,y)=0,$$

where $J_x$ and $J_y$ are the partial derivatives of J(x,y) with respect to mobile unit 106 coordinates x and y. If the instantaneous distance measurements $r_i$ are error-free, then the true position $(x_T, y_T)$ 414 of the mobile unit 106 will be a solution of this system. Two solutions that satisfy the criteria result in two possible locations including the true location $(x_T, y_T)$ 414 and an ambiguous location $(x_b, y_b)$ 416 which lie on opposite sides of the satellite ground track 404.

Newton's method finds a solution to equation (2) from an initial estimate $(x_0, y_0)$ of the mobile unit position by creating a sequence $(x_k, y_k)$ of positions which converge to a solution of equation (2). The iterative process uses the linear terms of a two-variable Taylor expansion to approximate the functions $J_x$ and $J_y$ in the vicinity of the most recent position in the sequence. In matrix-vector form this approximation is given by $$\begin{bmatrix} J_x(x,y) \\ J_y(x,y) \end{bmatrix} \cong \begin{bmatrix} J_x(x_k, y_k) \\ J_y(x_k, y_k) \end{bmatrix} + \begin{bmatrix} J_{xx} & J_{xy} \\ J_{yx} & J_{yy} \end{bmatrix} \begin{bmatrix} x - x_k \\ y - y_k \end{bmatrix}, \qquad (3)$$

where $J_{xx}$, $J_{xy}$, $J_{yx}$ and $J_{yy}$ are the second partial derivatives of J evaluated at the current position $(x_k, y_k)$. The next position $(x_{k+1}, y_{k+1})$ in the sequence is the one which causes the left side of (3) to become zero:

$$\begin{bmatrix} 0 \\ 0 \end{bmatrix} = \begin{bmatrix} J_x(x_k, y_k) \\ J_y(x_k, y_k) \end{bmatrix} + \begin{bmatrix} J_{xx} & J_{xy} \\ J_{yx} & J_{yy} \end{bmatrix} \begin{bmatrix} x_{k+1} - x_k \\ y_{k+1} - y_k \end{bmatrix}, \qquad (4)$$

This equation can also be written in the form $$\begin{bmatrix} 0 \\ 0 \end{bmatrix} = \begin{bmatrix} J_x(x_k, y_k) \\ J_y(x_k, y_k) \end{bmatrix} + \begin{bmatrix} J_{xx} & J_{xy} \\ J_{yx} & J_{yy} \end{bmatrix} \left( \begin{bmatrix} x_{k+1} \\ y_{k+1} \end{bmatrix} - \begin{bmatrix} x_k \\ y_k \end{bmatrix} \right) \qquad (5)$$

Solving for the $k+1^{st}$ position, we obtain $$\begin{bmatrix} x_{k+1} \\ y_{k+1} \end{bmatrix} = \begin{bmatrix} x_k \\ y_k \end{bmatrix} - \begin{bmatrix} J_{xx} & J_{xy} \\ J_{yx} & J_{yy} \end{bmatrix}^{-1} \begin{bmatrix} J_x(x_k, y_k) \\ J_y(x_k, y_k) \end{bmatrix} \qquad (6)$$

The partial derivatives of J in (6) are calculated at the position $(x_k, y_k)$ by differentiation of (1) to obtain $$J_x(x_k, y_k) = -2 \sum_{i=1}^{n} [r_i - d_i(x_k, y_k)] \frac{\partial d_i}{\partial x}(x_k, y_k) \qquad (7)$$

$$J_y(x_k, y_k) = -2 \sum_{i=1}^{2} [r_i - d_i(x_k, y_k)] \frac{\partial d_i}{\partial y}(x_k, y_k)$$

The second partial derivatives of J in (6), which are also calculated at the position $(x_k, y_k)$, are obtained by differentiation of the equations (7):

$$J_{xx} = -2 \sum_{i=1}^{n} \left\{ [r_i - d_i(x_k, y_k)] \frac{\partial^2 d_i}{\partial x^2}(x_k, y_k) - \left[ \frac{\partial d_i}{\partial x}(x_k, y_k) \right]^2 \right\} \qquad (8)$$

$$J_{xy} = J_{yx} =$$

$$-2 \sum_{i=1}^{n} \left\{ [r_i - d_i(x_k, y_k)] \frac{\partial^2 d_i}{\partial x \partial y}(x_k, y_k) - \frac{\partial d_i}{\partial x}(x_k, y_k) \frac{\partial d_i}{\partial y}(x_k, y_k) \right\}$$

$$J_{yy} = -2 \sum_{i=1}^{2} \left\{ [r_i - d_i(x_k, y_k)] \frac{\partial^2 d_i}{\partial y^2}(x_k, y_k) - \left[ \frac{\partial d_i}{\partial y}(x_k, y_k) \right]^2 \right\}$$

After two instantaneous distance measurements 421, 422 have been made (the minimum number required to establish a position), the positioning algorithm is, preferably, repeated to update the estimate of the mobile user position as the number n of distance measurements 423–426 increases. Each repeat uses all distance measurements (421–426) received up to the current time. Assuming one instantaneous distance measurement 421–426 per second, the speed of the positioning algorithm is more than sufficient to recalculate the mobile unit location $(x_T, y_T)$ 414 each time a new instantaneous distance measurement (421–426) is made. The updates may be made less frequently, however, such as one update for every 10 new instantaneous distance measurements (421–426).

Before the algorithm can make its first position estimate, it must be supplied with an initial position estimate $(x_0, y_0)$ 428. The choice is not critical, but should be in the general vicinity (perhaps within 200–300 km) of the mobile unit location $(x_T, y_T)$ 414. A reasonable choice is a point 428 that is approximately 100 km to 200 km on one side of the satellite ground track 404 with the closest point on the ground track 404 directly below the satellite 102 at the time of the first distance measurement 421. For the position updates using additional data, the algorithm should be initialized with the previously obtained position estimate to reduce the convergence time.

Each time the positioning algorithm is run, a stopping criterion is needed to determine when adequate convergence has been achieved. The preferred approach includes stopping the iterations when the position estimates become essentially static. This is achieved by measuring the change in position estimate from one iteration to the next and stopping the algorithms when the magnitude of the change falls below a predetermined threshold. An alternate technique of determining the stopping point includes performing a fixed number of iterations that is large enough to guarantee convergence under all conditions.

Computer simulations indicate that for the first run of the algorithm (using two range measurements), 20 iterations is always sufficient. On the other hand, when the algorithm is providing position updates with additional data, three iterations are sufficient because the algorithm is being initialized with previous position estimates which are already close to the position solution. Therefore, an alternate approach includes performing 20 iteration for the first position estimate and 3 iterations for each of the position updates.

Even with a large number n of measurements (n might be as large as 250), a typical personal computer (PC) can perform the iterations required for convergence to each new position update in less than a few hundredths of a second. This represents a light computational load, especially if performed at a terrestrial station where a great amount of computational horsepower is available.

An alternate algorithm for minimizing $J(x,y)$ in (1) includes the gradient descent technique. This approach moves the position $(x,y)$ in a direction in which $J(x,y)$ decreases the most rapidly, and stops when $J(x,y)$ can no longer be decreased. Although it is somewhat simpler than Newton's method, it is not as robust. Stable versions generally take much longer to converge. Although any one of several other known related descent algorithms may be used, Newton's Method is preferred. Further, recursive algorithms such as Kalman filters or recursive least-squares methods may be used to increase the efficiency of computation. In the preferred embodiment, however, the computational load of Newton's method is so light that little real benefit would be gained by using such algorithms. Additionally, Newton's method is mathematically simpler and is very robust. By contrast, methods using such common filters often require considerable effort to make them numerically stable.

Because the orbital path 110 of the satellite 102 closely approximates a straight line during the instantaneous distance measurement process, there will generally be two user locations on opposite sides of the satellite ground track 404 which would produce similar range measurement sequences. As a consequence $J(x,y)$ will have a local minimum, i.e. $J_x=J_y=0$, at each of these locations and equation (2) will have two solutions. Newton's algorithm will therefore converge to one of the two possible solutions of equation (1), depending on the initial choice of position $(x_0,y_0)$ supplied to the algorithm.

If the satellite 102 initiates the signal pulses and computes the instantaneous distances 421–426 to the mobile unit 106 as the pulses are returned, then the instantaneous distance measurements $r_i$, 421–426 appearing in equation (1) are computed as follows:

$$r_i = \frac{t_R - t_T - t_D}{2c} \tag{9}$$

where $t_T$ is the time of transmission of the pulse from the satellite 102, $t_R$ is the time of reception at the satellite 102 of the retransmitted signal from the mobile unit 106, $t_D$ is the retransmission delay of the mobile unit 106, and c is the speed of light ($3\times10^8$ meters/second).

On the other hand, if the ranging pulses are initiated from and returned to the ground station as in the second alternate embodiment, the instantaneous distance measurements $r_i$ 421–426 are computed as follows:

$$r_i = \frac{t_R - t_T - t_{p1} - t_{s1} - t_{p2} - t_{s2}}{2c} \tag{10}$$

where $t_T$ is the time of transmission of the pulse from the ground station, $t_R$ is the time of reception at the ground station of the retransmitted pulse from the mobile unit 106, $t_{p1}$ and $t_{p2}$ are the respective outgoing and incoming propagation delays between the terrestrial station 108 and the satellite 102 visible to the mobile unit 106, and $t_{s1}$ and $t_{s2}$ are the respective total outgoing and incoming switching delays through the satellite chain including the retransmission delay of the mobile unit 106. Using known techniques, the propagation delays are computed at the terrestrial station 108 by tracking the locations of the satellites 102. The switching delays are presented to the terrestrial station 108 by time tagging each pulse with the delay.

The distance functions $d_i(x,y)$ appearing in equation (1) are computed from the formula $$d(x,y)=\sqrt{(x_s-x)^2+(y_s-y)^2+(z_s-z(x,y))^2}=\sqrt{u}, \tag{11}$$

where, for convenience in what follows, we have defined $$u=(x_s-x)^2+(y_{s-y})^2+(z_s-z(x,y))^2. \tag{12}$$

In these expressions, $(x_s,y_s,z_s)$ and $(x,y,z(x,y))$ are the respective satellite 102 and mobile unit 106 positions at the time the distance is computed (this time is identified by the subscript i on $d(x,y)$, which has been omitted for simplicity). Note that the mobile unit's 106 z-coordinate is expressed as a function of x and y. This function is the topographic data (terrain function) stored at the terrestrial station 108 which gives the mobile unit's 106 altitude z as a function of horizontal position.

The various partial derivatives of J in equations (7) and (8) depend on partial derivatives of the distance function $d(x,y)$. Differentiating equation (11) we obtain $$d_x=\tfrac{1}{2}u^{-\frac{1}{2}}u_x$$

$$d_x=\tfrac{1}{2}u^{-\frac{1}{2}}u_y$$

$$d_{xx}=\tfrac{1}{2}u^{-\frac{1}{2}}u_{xx}-\tfrac{1}{4}u^{-\frac{3}{2}}(u_x)^2 \tag{13}$$

$$d_{yy}=\tfrac{1}{2}u^{-\frac{1}{2}}u_{yy}-\tfrac{1}{4}u^{-\frac{3}{2}}(u_y)^2$$

$$d_{xy}=d_{yx}=\tfrac{1}{2}u^{-\frac{1}{2}}u_{xy}-\tfrac{1}{4}u^{-\frac{3}{2}}u_xu_y$$

The first and second partial derivatives of u appearing in the above expressions are calculated by differentiation of equation (12):

$$u_x=2[x-x_s+(z(x,y)-z_s)z_x]$$

$$u_y=2[y-y_s+(z(x,y)-z_s)z_y]$$

$$u_{xx}=2[1+(z(x,y)-z_s)z_{xx}+z_x^2] \tag{14}$$

$$u_{yy}=2[1+(z(x,y)-z_s)z_{yy}+z_y^2]$$

$$u_{xy}=u_{yx}=2[1+(z(x,y)-z_s)z_{xy}+z_xz_y]$$

Figure 5A:
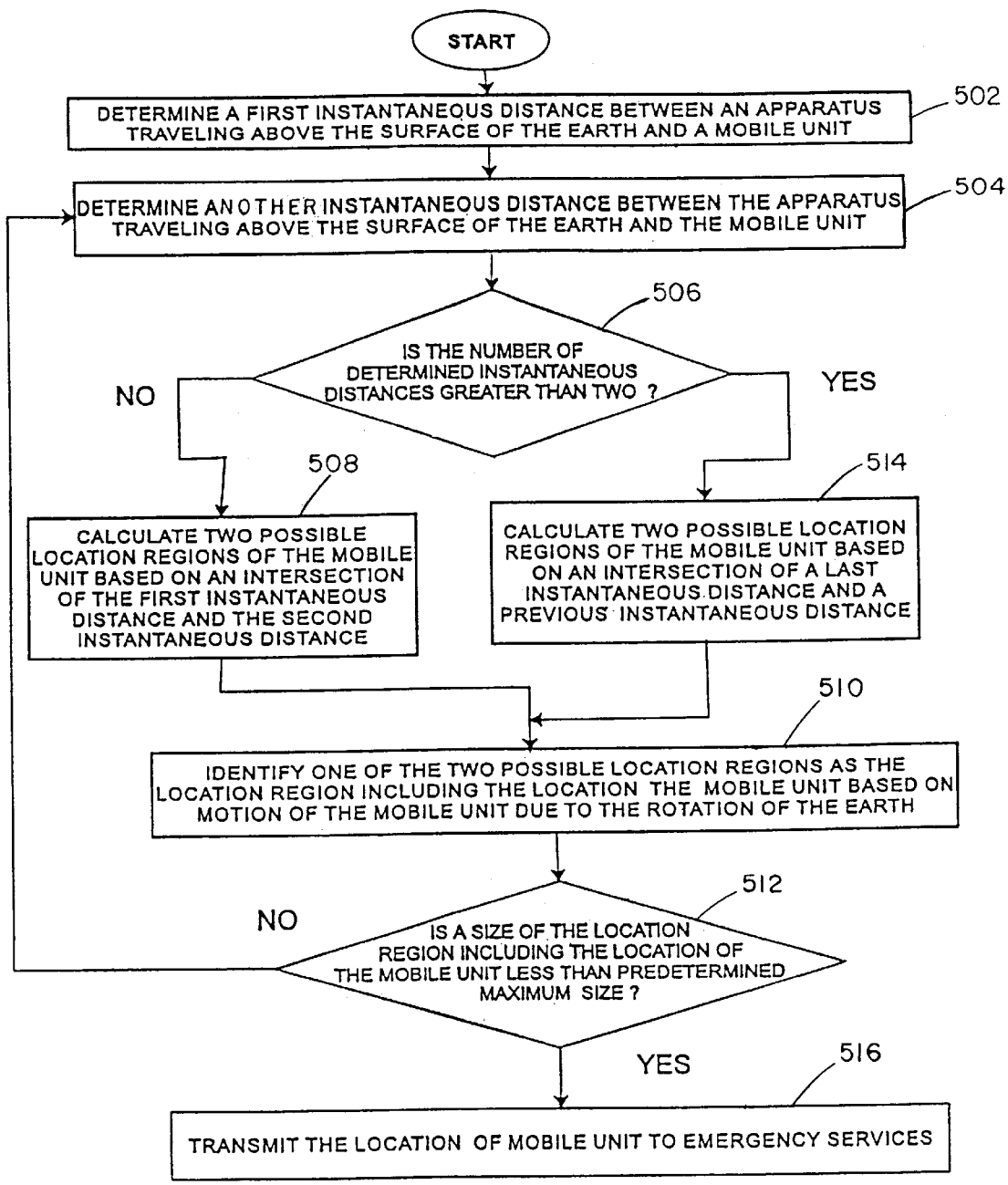
FIG. 5a is a flow chart of a method of locating a mobile unit in accordance with the preferred embodiment of the present invention.

FIG. 5a is a flow chart of a method of determining the location 414 of the mobile unit 106 in accordance with the preferred embodiment of the invention. In the preferred embodiment, the calculations and decisions of the method are performed within the terrestrial station 108. As discussed above however, the calculation may be performed within the apparatus (satellite) 102 or any other processor or computer coupled to the system 100. In the preferred embodiment, the various steps of determining the location of the mobile unit 106 are performed using the location algorithm discussed above. Although the functional blocks discussed in reference to FIGS. 5a, and 5b correspond to a geometrical representation, those skilled in the art will recognize that the implementation of the preferred embodiment using the location algorithm results in a method of minimizing the squares of the errors of a plurality of distance measurements defining the location of the mobile unit 106 and does not directly correspond to various steps in the flow chart. Accordingly, the steps of determining the location regions of the mobile unit 106 do not directly correspond to an equation of the location algorithm. However, the implemented location algorithm performs the function of determining the location of the mobile unit 106 which can be geometrically explained and represented as in FIGS. 3b through 5b.

At step 502, the first instantaneous distance between the apparatus 102 traveling above the surface of the earth and the mobile unit 106 is determined. As discussed below in reference to FIG. 5b, the apparatus 102 receives a signal from the mobile unit 106 to determine the instantaneous distance. In the preferred embodiment, the signal is transmitted from the apparatus 102 to the mobile unit 106 before the mobile unit 106 retransmits the signal back to the apparatus 102 after a predetermined retransmission delay.

At step 504, the second (another) instantaneous distance between the apparatus 102 and the mobile unit 106 is determined. In the preferred embodiment, the second signal is determined by a method similar to the method of determining the first instantaneous distance.

At step 506, it is determined whether more than two instantaneous distances have been determined. If more than two instantaneous distances have been determined, the method proceeds to step 514. If only two instantaneous distances have been determined, the method continues at step 508.

Two possible location regions of the mobile unit 106 are calculated at step 508. The location regions are calculated based on the intersection between the first instantaneous distance and the second instantaneous distance. Although the location regions may be the points defined by the intersection of the two instantaneous distances, the location regions are not necessarily the intersections and may define a small geographical region that has a substantial probability of including the location of the mobile unit 106.

At step 510, one of the two possible location regions is identified as the location region that includes the location of the mobile unit 106. The motion of the mobile unit 106 due to the rotation of the earth is observed to determine which of the two locations contains the mobile unit 106. As discussed below in reference to FIG. 5c, the location algorithm will result in smaller residual values for the location region that includes the location of the mobile unit 106 in the preferred embodiment.

At step 512, it is determined whether the size of the location region including the mobile unit 106 is less than a predetermined maximum size. In other words, at step 512, it is determined whether the required resolution has been achieved. In the preferred embodiment, the number of measurements corresponds to a particular resolution. The size of the location region is inversely proportional to the number of instantaneous distance measurements. The relationship between the two values is not necessarily linear and is dependent on the particular system characteristics. Those skilled in the art will recognize the various factors that determine the number of measurements for acquiring a particular resolution which will depend on noise and power levels and other system parameters. If the size of the location region is less than the predetermined maximum size, the method proceeds to step 516 where the location of the mobile unit 106 is transmitted to emergency services 222.

If the location region is not less than the predetermined maximum size, the method returns to step 504 where another instantaneous distance is determined.

At step 514, two possible location regions of the mobile unit 106 are calculated based on the last instantaneous distance measured and at least one previously determined instantaneous distance (previous instantaneous distance). In the preferred embodiment, however, all instantaneous distances that have been determined are used to calculate the two location regions. As discussed above in reference to FIG. 4, the location algorithm utilizes a plurality of instantaneous distance measurements to converge to a location region. As the number of instantaneous distance measurements increases the size of the location region decreases. Accordingly, the method continues to repeat steps 504 through 512 until it is determined, at step 512, that the size of the location region is less than the predetermined maximum size. Graphically, the plurality of instantaneous distances intersect to provide a plurality of intersections.

Figure 5B:
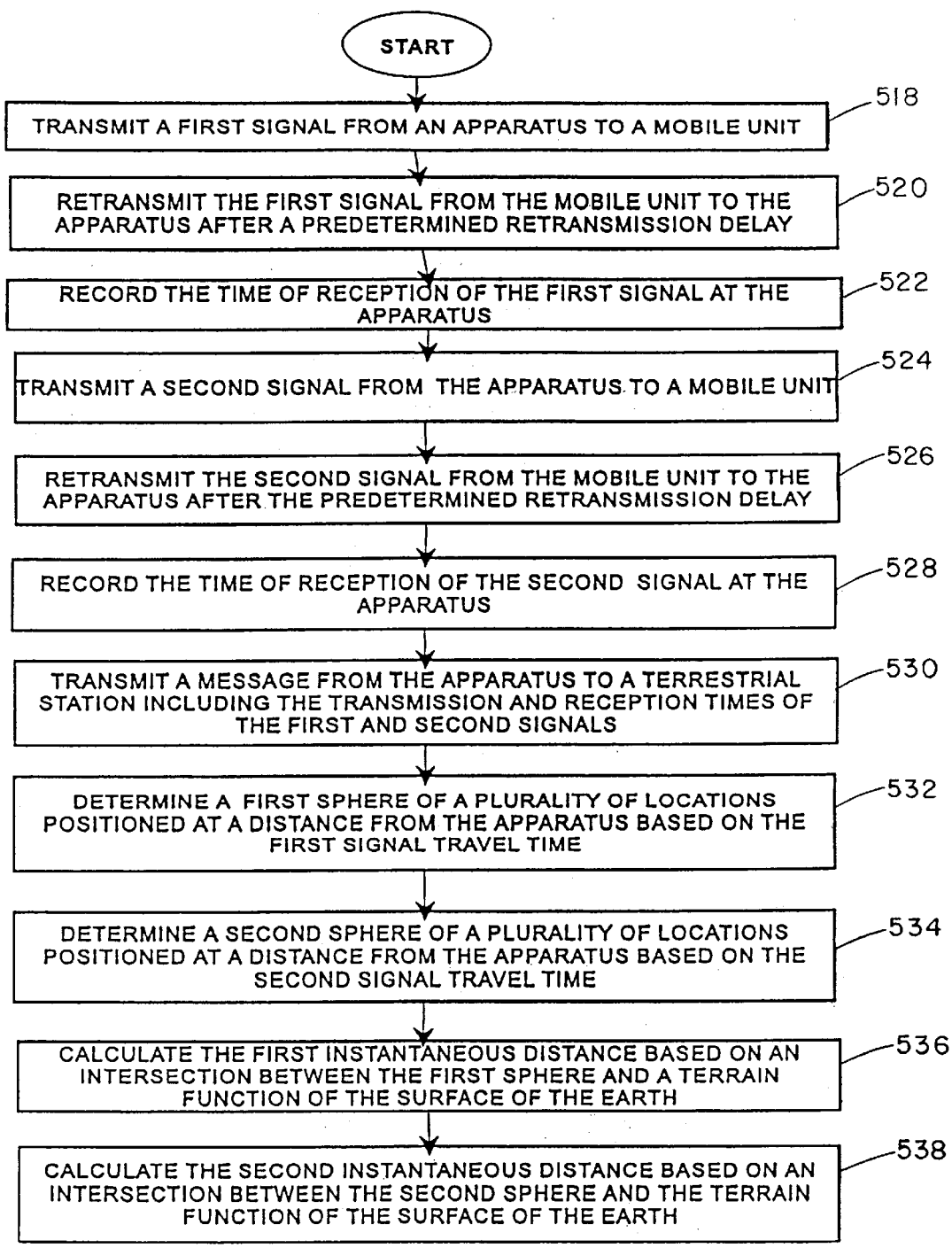
FIG. 5b is a flow chart of a method of determining the first and second instantaneous distances in accordance with the preferred embodiment of the invention.

FIG. 5b is flow chart of a method of determining the first instantaneous distance (step 502) and the second instantaneous distance (step 504) in accordance with the preferred embodiment of the invention. At step 518, the apparatus (satellite) 102 transmits the first signal to the mobile unit 106 at a first signal transmission time.

The signal is received by the mobile unit 106 at step 520 and retransmitted to the apparatus (satellite) 102 after a predetermined retransmission delay. As discussed above, the retransmission delay is maintained at a consistent minimum value.

At step 522, the apparatus 102 receives the retransmitted first signal at a first signal reception time and records the reception time.

At step 524, the apparatus 102 transmits a second signal at a second signal transmission time to the mobile unit 106.

The second signal is received at the mobile unit 106 and retransmitted to the apparatus after the predetermined retransmission delay at step 526.

At step 528, the apparatus 102 receives the second signal at a second signal reception time and records the reception time.

At step 530, the apparatus 102 transmits a message containing the first signal transmission time, the first signal reception time, the second signals transmission time and the second signal reception time to the terrestrial station.

As discussed above, the travel times of the signal may be relayed to the terrestrial station 108 in any one of various methods. For example, the signal travel times may be calculated at the apparatus and transmitted to the terrestrial station 108 as a time difference rather than a transmission time and a reception time.

At step 532, the terrestrial station 108 determines the first sphere 320 of a plurality of locations positioned at a distance from the apparatus 102 based on the difference between the first signal transmission time and the first signal reception time. As discussed above, the first signal travel time is calculated by subtracting the retransmission delay of the mobile unit 106 from the difference of the first signal transmission time and the first signal reception time and dividing the result by two. Multiplying the first signal transmission time by the speed of light results in a distance between the apparatus 102 and the mobile unit 106. This distance defines a plurality of locations positioned on a sphere 320 having center at the location 304 of the apparatus 102 at the first reception time and a radius 308 equal to the distance.

At step 534, a second sphere 322 of a plurality of locations positioned at a distance from the apparatus 102 based on the second signal travel time. The second signal travel time is calculated by subtracting the retransmission delay of the mobile unit 106 from the difference of the second signal transmission time and the second signal reception time and dividing the result by two. Multiplying the second signal transmission time by the speed of light results in a distance between the apparatus 102 and the mobile unit 106. This distance defines a plurality of locations positioned on a sphere 322 having center at the location 306 of the apparatus 102 at the second reception time and a radius 310 equal to the distance.

At step 536, the first instantaneous distance is calculated based on the intersection between the first sphere 320 and the terrain function of the surface of the earth 104. Geometrically, the intersection of the first sphere 320 and the terrain function of the earth 104 results in a substantially circular plurality of locations lying on the surface of the earth 104. The geometric shape of the plurality of possible locations approaches a circle as the terrain function tends to describe a flat plane. In other words, elevation differences on the surface of the earth 104 distort the circular shape of the plurality of possible locations of the mobile unit 106 on the earth's 104 surface.

At step 538, the second instantaneous distance is calculated based on the intersection between the second sphere 322 and the terrain function of the surface of the earth 104. Similarly to the first sphere 320, the intersection of the second sphere 322 and the terrain function of the earth 104 results in a substantially circular plurality of locations lying on the surface of the earth 104. The geometric shape of the plurality of possible locations approaches a circle as the terrain function tends to describe a flat plane.

Figure 5C:
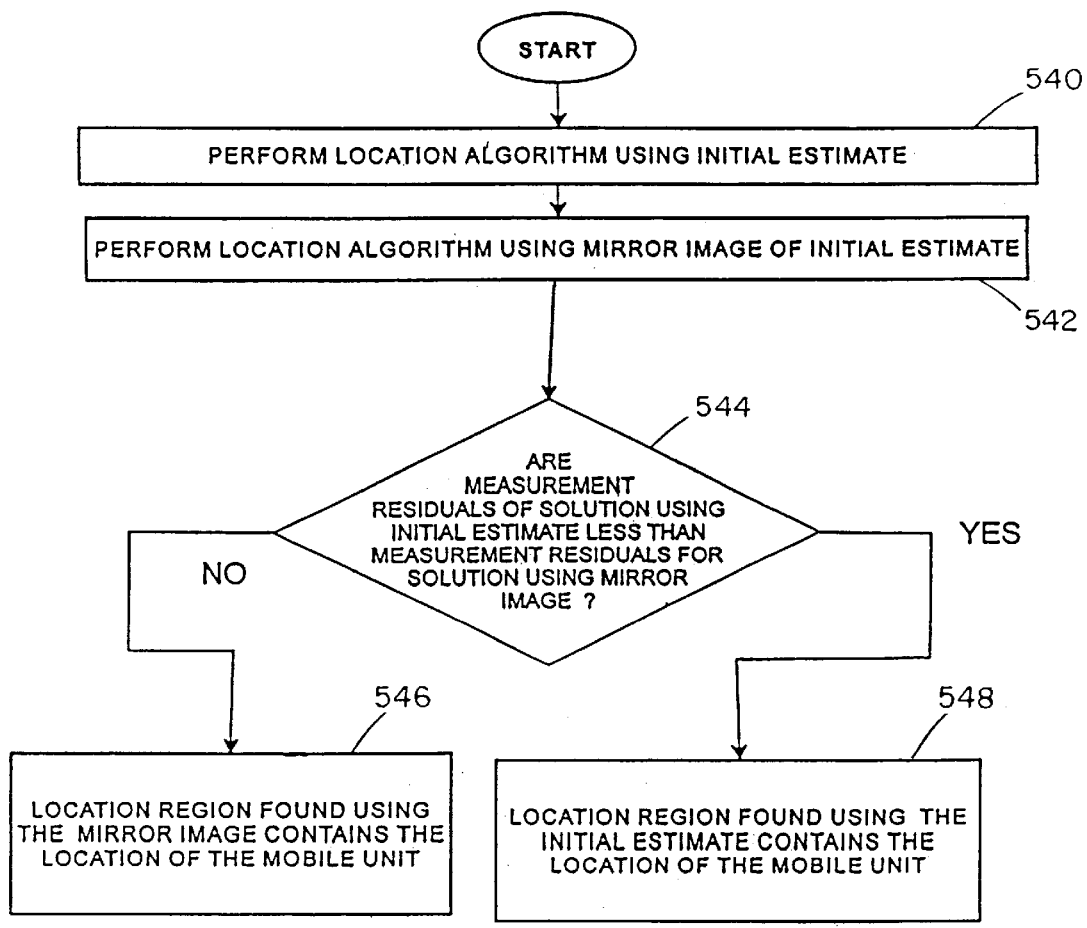
FIG. 5c is a flow chart of a method of resolving the lateral ambiguity of the mobile unit location in accordance with the preferred embodiment of the invention.

FIG. 5c is a flow chart of a method of determining the location 414 of the mobile unit 106 in accordance with the preferred embodiment of the invention. Rotation of the earth 104 causes the orbital path 110 of the satellite 102 to have some amount of lateral asymmetry as seen from the ground. This asymmetry causes one of the two solutions to be "better" than the other in the sense that the sequence of measured distances 421–426 will better fit what should be observed at that location [i.e., a smaller value of J(x,y)]. Accordingly, in the preferred embodiment, the location algorithm is performed using an initial estimate to determine a first position solution. A mirror image of the first position solution is used as the initial estimate to determine a second position solution. The values of measurement residuals for both location solutions are compared to determine the correct solution.

At step 540, the location algorithm is performed using an initial position estimate $(x_0, y_0)$ 428 and allowing it to converge to one of the two solutions denoted by $(x_a, y_a)$. The local minimum value of $J(x,y)$ is $J_a$, where $J_a = J(x_a, y_a)$.

At step 542, the location algorithm is performed using a mirror image $(x_a, -y_a)$ of the previously obtained position estimate $(x_a, y_a)$ as a second initial estimate where the mirror image $(x_a, -y_a)$ is located on the opposite side of the ground track 404. Since the mirror image $(x_a, -y_a)$ is very close to the second solution of the algorithm, the algorithm will converge to the second solution $(x_b, y_b)$ where $J_b = J(x_b, y_b)$.

At step 544, $J_a$ is compared to $J_b$ to determine if $J_a < J_b$. If $J_a < J_b$ then the method proceeds to step 548 where it is determined that the first location estimate $(x_a, y_a)$ of the mobile unit 106 (found using the initial estimate) contains the "true" location of the mobile unit 106. Therefore, the measurement residuals of the solution using the initial position estimate $(x_0, y_0)$ 428 are compared to the measurement residuals of the solution using the mirror image $(x_a, -y_a)$ of the solution found using the intial estimate $(x_0, y_0)$ 428.

If $j_a > J_b$, then the method proceeds to step 546 where it is determined that the location of the mobile user 106 is contained with the second location region estimnate $(x_b, y_b)$ found using the mirror image $(x_a, -y_a)$ of the first location region estimate $(x_a, y_a)$.

TYPICAL PERFORMANCE EXPECTATION FOR THE PREFERRED EMBODIMENT

Computer simulations have been performed to assess the performance potential of the method of locating a mobile unit 106 in accordance with the preferred embodiment of the invention. Those skilled will recognize that the following results may not include all sources of error. The following conditions are assumed: The satellite 102 altitude is 800 km judged to be typical of LEO constellations). Two-way pulse (or wideband) instantaneous distance measurements 421–426 with an RMS error of 5 meters (judged a reasonable value, comparable to GPS) are performed every second, and the mobile unit 106 altitude uncertainty is 30 meters RMS. A 2000 km by 2000 km service area is assumed, which is centered at the satellite ground track 404 location at the time signal measurements are initiated.

Figure 6:
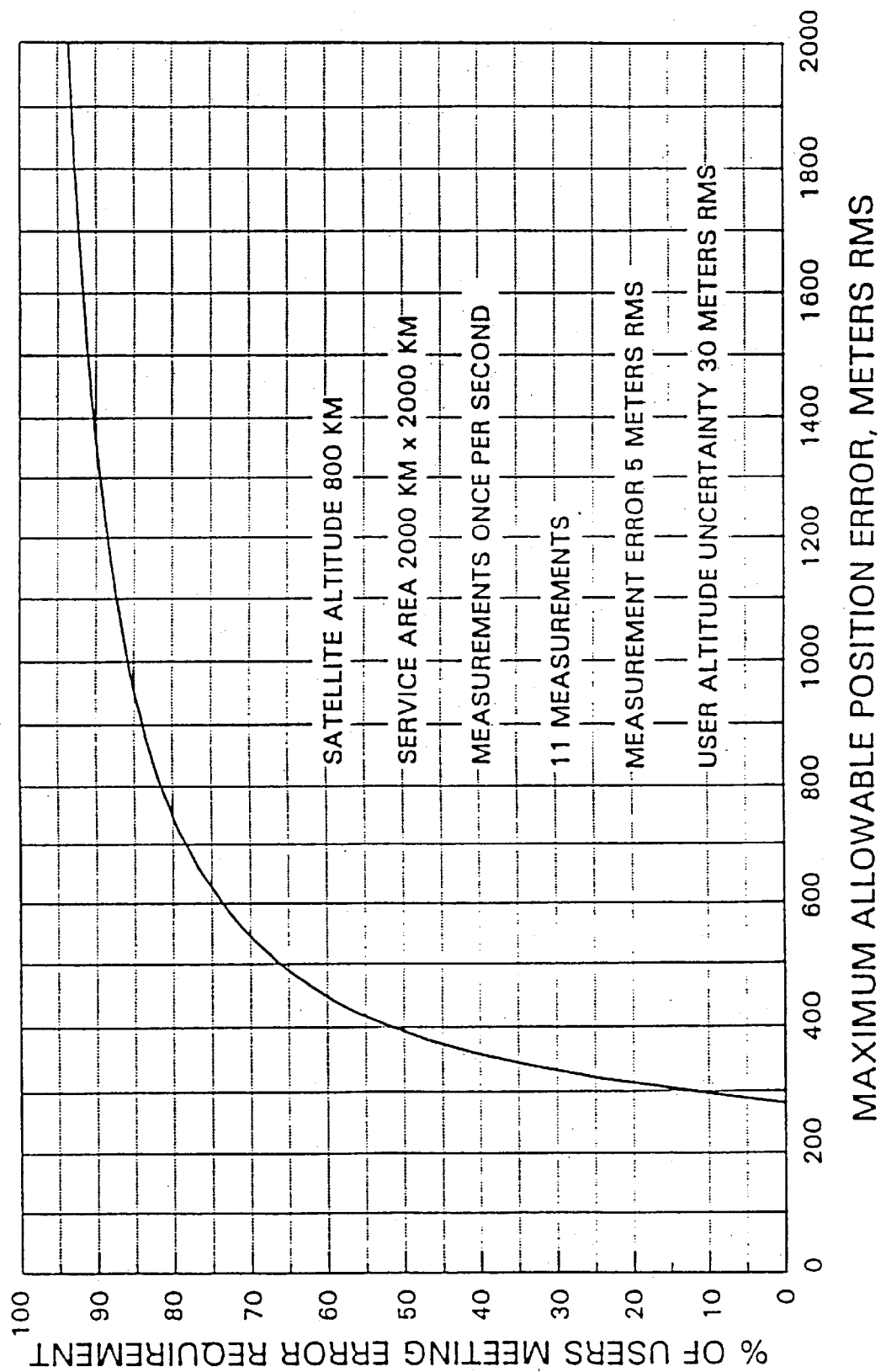
FIG. 6 is graphical representation of a simulation of the method locating the mobile unit in accordance with the preferred embodiment of the invention where the number of instantaneous distance measurements is eleven.
Figure 7:
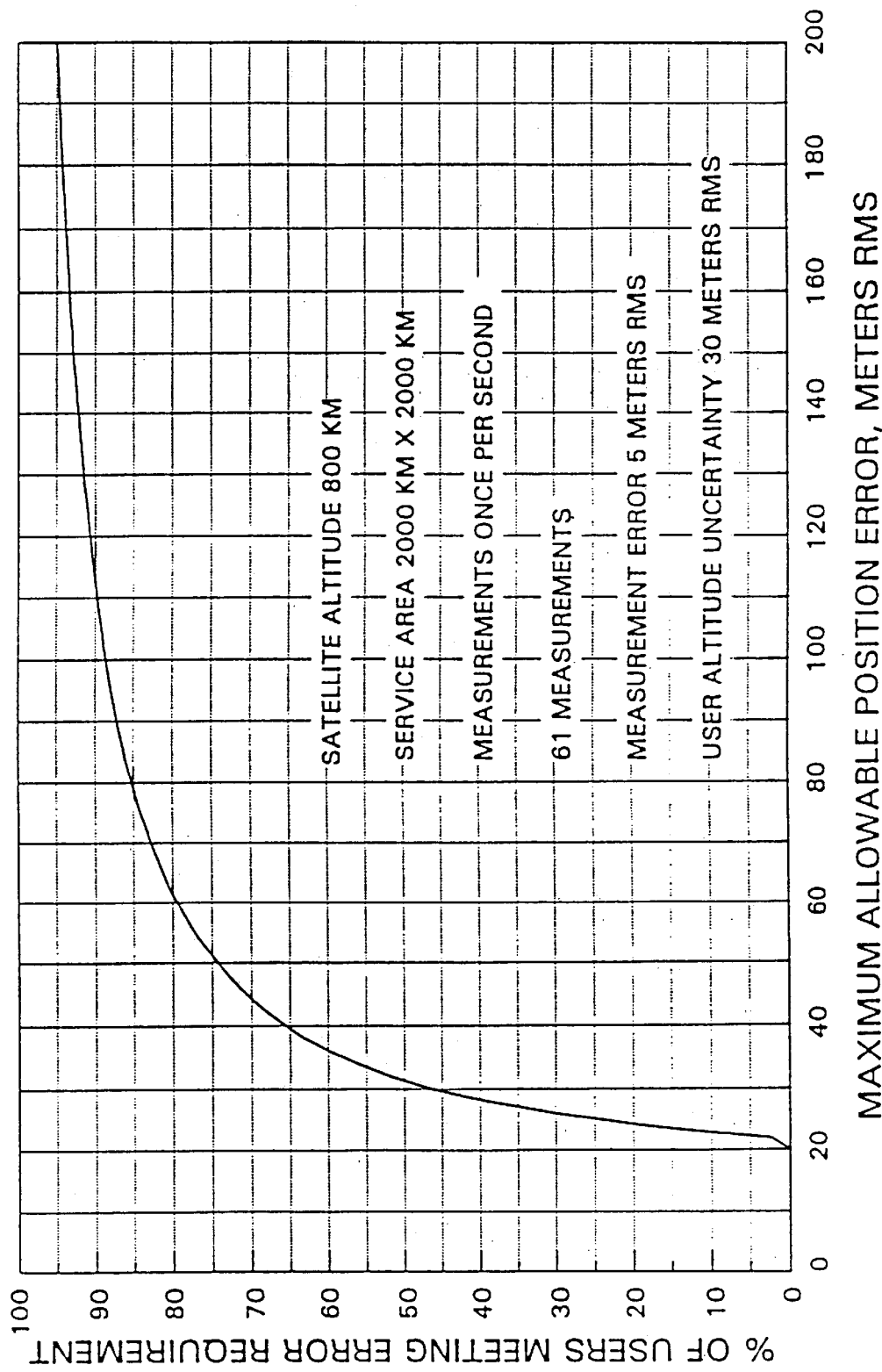
FIG. 7 is graphical representation of a simulation of the method locating the mobile unit in accordance with the preferred embodiment of the invention where the number of instantaneous distance measurements is 61.
Figure 8:
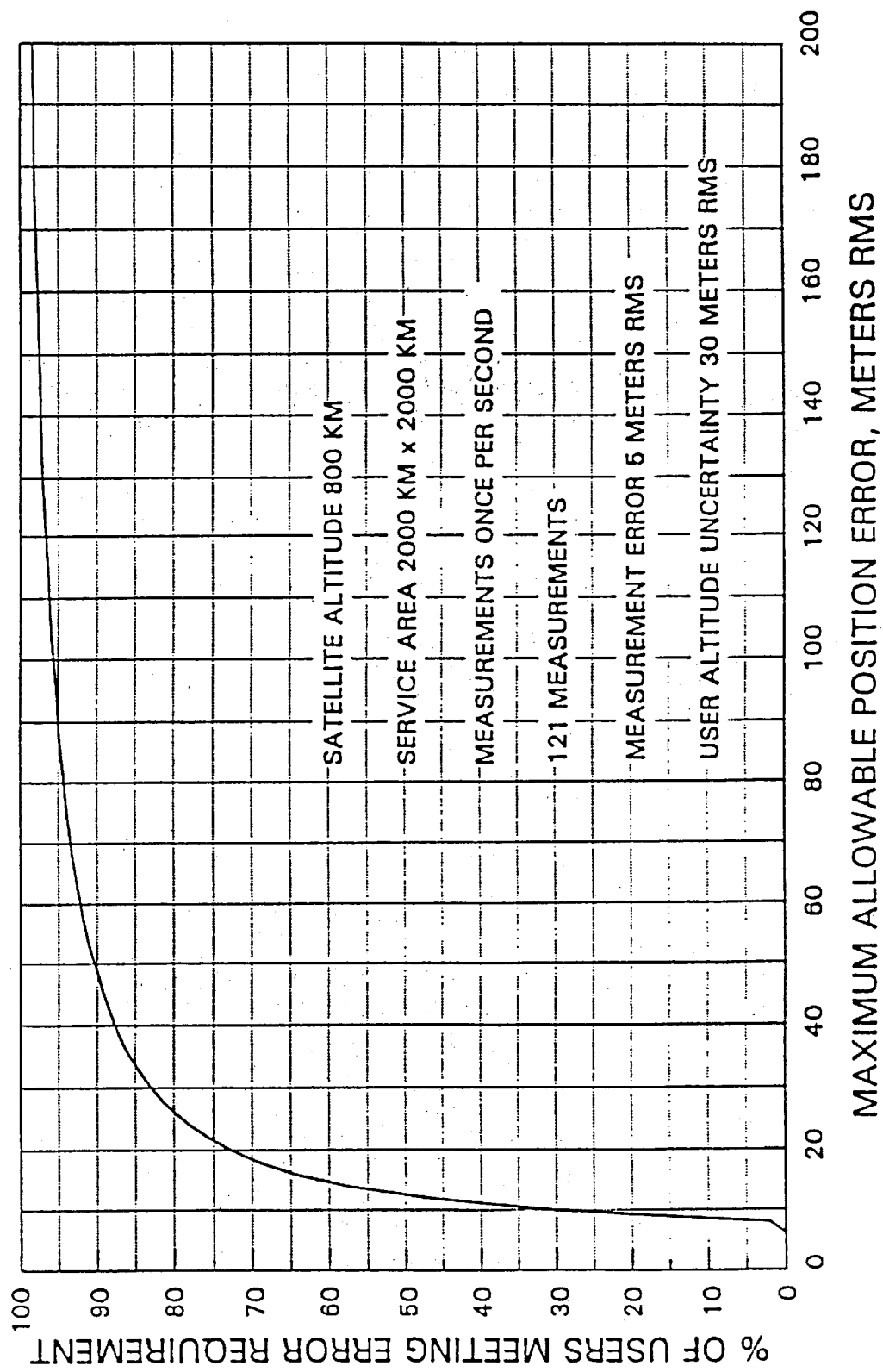
FIG. 8 is graphical representation of a simulation of the method locating the mobile unit in accordance with the preferred embodiment of the invention where the number of instantaneous distance measurements is 121.

Each of FIGS. 6, 7, and 8 show the probability (expressed in percent) that the position (x,y) of a mobile unit 106 randomly situated in the service area will be determined with less than the allowable RMS positioning error shown on the horizontal axis using the method of locating the mobile unit 106 in accordance with the preferred embodiment of the invention. All parameters for FIGS. 6, 7, and 8 are the same except for the accumulated measurement times, which are 10, 60, and 120 seconds, respectively (11, 61, and 121 two-way distance measurements). These results assume that lateral ambiguity resolution has been correctly determined.

Figure 9:
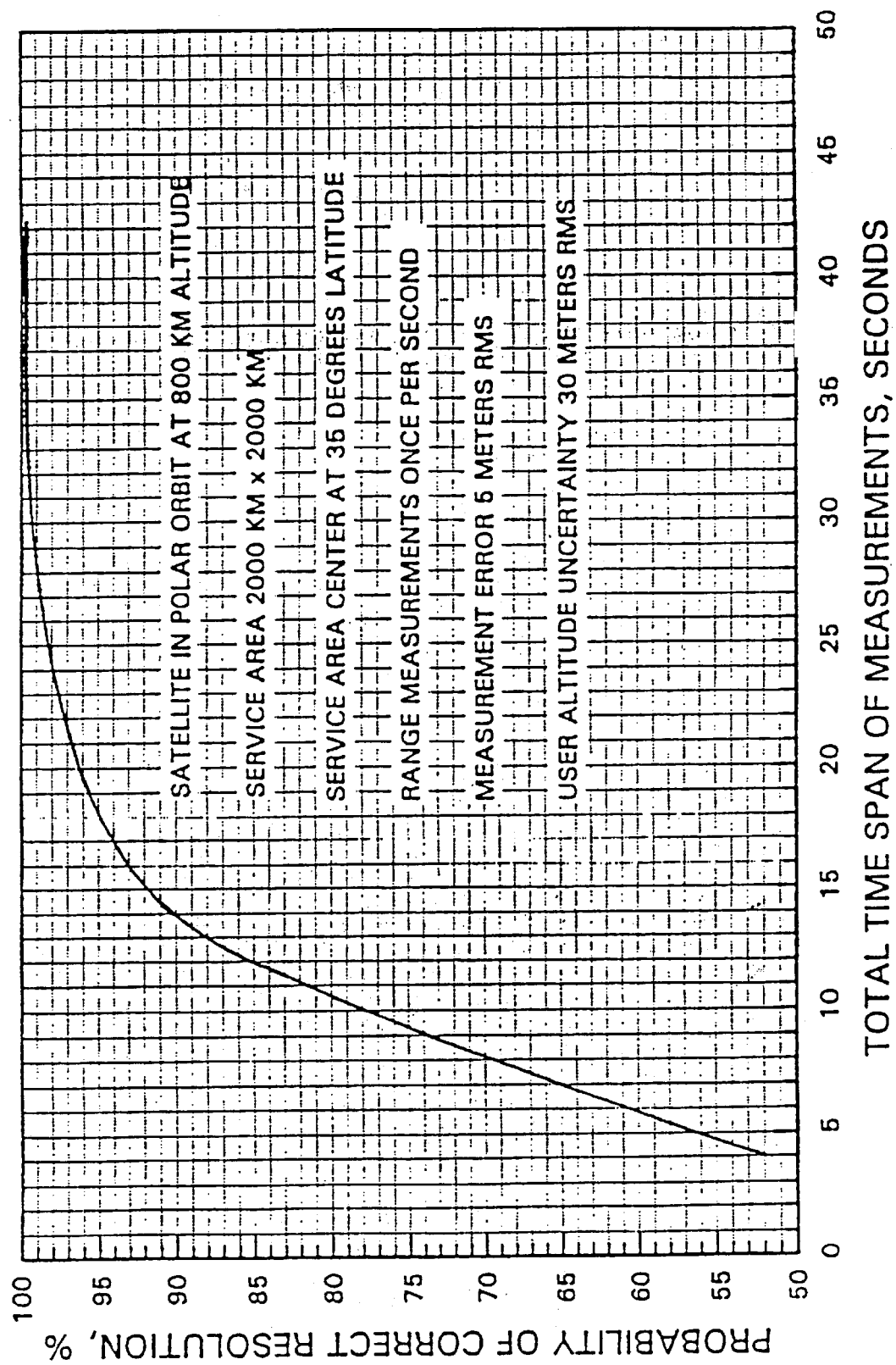
FIG. 9 is graphical representation of a simulation of the method resolving the lateral ambiguity of the mobile unit in accordance with the preferred embodiment of the invention.

FIG. 9 is graphical representation of a the lateral ambiguity resolution performance of the method of locating 414 a mobile unit 106 in accordance with the preferred embodiment. Analysis and simulations have been performed to determine how reliably the earth's 404 rotation can be used to resolve what would otherwise be the inherent lateral ambiguity of a single-satellite 102 determination of a mobile unit location 414. Ambiguity resolution performance generally improves with increasing inclination angle of the satellite orbit path 110, increasing latitude of the mobile unit 106, and increasing time span of the instantaneous distance measurement process. Performance does not depend strongly on the inclination of the satellite orbit path 110 for inclination angles greater than about 60 degrees.

A typical ambiguity resolution performance curve is shown in FIG. 9 for a polar satellite orbit at 800 km altitude in a 2000 km×2000 km service area aligned with the satellite ground track. The center of this area is the satellite ground track 404 location when instantaneous distance measurements are started, and is assumed to be at 35 degrees North (or South) latitude. It is also assumed that two-way range measurements are made once per second, with a 5 meter RMS error in each measurement, and that the mobile unit 106 altitude uncertainty is 30 meters RMS. The vertical axis of the graph in FIG. 9 shows the probability of a successful lateral ambiguity resolution for a given time span if the mobile unit 106 is randomly positioned in the service area (with a uniform probability distribution). As shown in FIG. 9, there is a minimum waiting time before reliable ambiguity resolution can be achieved, which is on the order of 15 seconds. However, within 30 seconds or so, correct ambiguity resolution will occur for about 99% of the mobile units 106. The highest likelihood of failure occurs for mobile unit 106 unfortunate enough to be near the ground track 404 of the satellite, where the poor geometric dilution of precision (GDOP) can cause unacceptably large positioning errors.

SINGLE TRANSMISSION PATH ALTERNATE EMBODIMENTS

In a third alternate embodiment of the invention, the mobile unit transmits a plurality of signals to an apparatus (satellite) 102 traveling above the surface of the earth 104. In comparison to the preferred embodiment, the signals do not originate at the satellite 102. The architecture of the system is similar to the architecture described above in regard to the preferred embodiment except that the clock 205 in the mobile unit 106, the clock 216 in the apparatus 102, and the clock (not shown) in the terrestrial station 108 should be much more accurate than in the preferred embodiment and should typically have an error of no more than 1 part per million.

The method of determining the geographic location of the mobile unit 106 in accordance with the third alternate embodiment is similar to the preferred method described above in regard to FIG. 5a. In an emergency situation, the user of the mobile unit 106 initiates transmission of a plurality of signals from the mobile unit 106 by activating the switch 202. When the switch 202 is activated, a controller 204 obtains a user identification number, and signal information from memory 208. The signal information includes signal frequency, signal duration and other parameters required to transmit the plurality of signals to the satellite 102. The transmitter that is part of a transceiver 210 transmits the plurality of signals to the satellite 102.

In the third alternate embodiment of the invention at least four signals are sent from the mobile unit 106 to the satellite 102. The time between transmission times may range from approximately 10 milliseconds to 1000 milliseconds and depends on several factors. The optimum timing of the transmission times depends on the particular satellite communication system 100 and parameters such as maximum time allowed for determining the location of the mobile unit, the desired accuracy of the estimated location, the speed of the satellite, the strength of the signals, the accuracy of the clocks (295, 216), the mobile unit retransmission delay, the maximum anticipated distance traveled by the signals and other factors that will be recognized by those skilled in the art. The duration of the signals also depends on these factors and is approximately 0.1 to 1.0 ms long.

Although only four signals are required to locate the mobile unit 106 (three to determine two possible locations of the mobile unit and a fourth to resolve the lateral ambiguity), additional signals are continuously transmitted by the mobile unit 106 to produce a more accurate result by receiving multiple signals at the satellite 102.

The satellite 102 receives the plurality of signals through a receiver within he transceiver 212 in the satellite 102. As will be explained in further detail below, the controller 214 in the satellite 102 transmits messages to the terrestrial station 108 through the transceiver 212. Also, as discussed below, a lock 216 determines reception times of the plurality of signals.

The messages from the satellite 102 are received by a receiver within the transceiver 218 in the terrestrial station 108. A controller 220 in the terrestrial station 108 determines the location of the mobile unit 106 based on the reception times transmitted by the satellite 102 in the messages.

The terrestrial station 108 forwards the location of the mobile unit 106 to emergency services 222 which may include fire, rescue, police or other services. Preferably, the terrestrial station communicates with emergency services 222 through a PSTN. Other infrastructures, however, may be used to transmit the location of the mobile unit such a cellular communication system, point to point microwave systems, or radio frequency communication systems.

Figure 10:
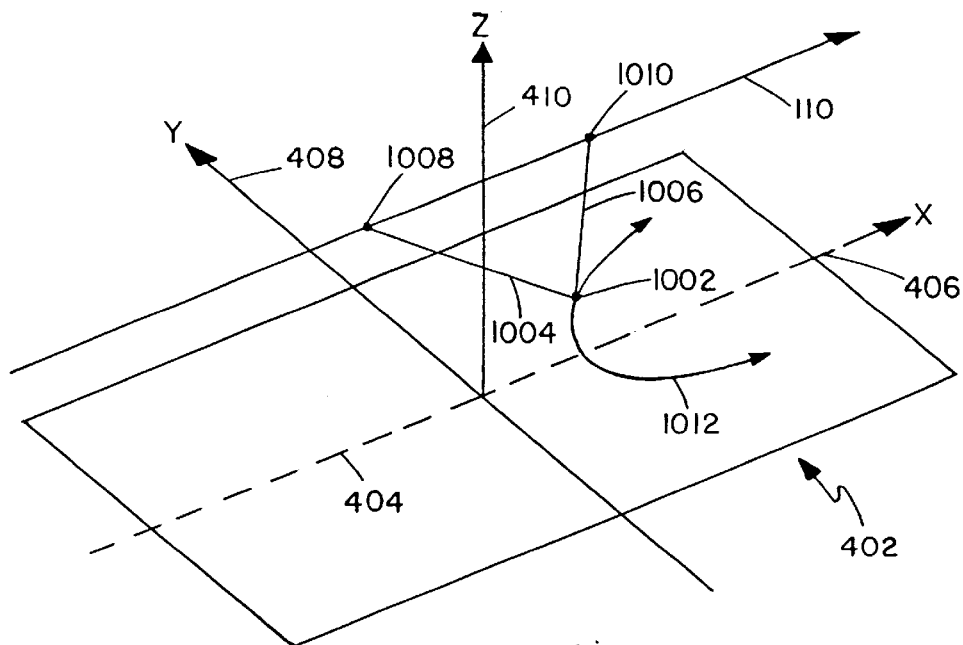
FIG. 10 is an isometric view of the apparatus traveling above the surface of the earth in accordance with the third and fourth alternate embodiments of the invention.

FIG. 10 is an isometric diagram of the apparatus 102 traveling above the surface of the earth in accordance with the third alternate embodiment of the invention. The apparatus 102 travels in the orbital path 110 that is parallel to the x axis 406 and intersects the z axis 410 at an altitude, h. The first signal is received by the satellite 102 at a reception time that corresponds to a first reception point, $(x_1, 0, h)$ 1008 along the orbit path 110. The second signal is received by the satellite 102 at a second reception time that corresponds to a second reception point $(x_2, 0, h)$ 1010. The first and second reception times are represented respectively by $t_1$ and $t_2$ and the time interval between the transmission times of the signals is represented by T. The mobile unit 106 is located at (x, y, 0) 1002 on the surface (402) of the earth 104. The distance 1004 between the first reception point 1008 and the mobile unit 102 location 1002 is the distance traveled by the first signal and the distance 1006 between the second reception point 1010 and the mobile unit location 1002 is the distance traveled by the second signal.

If k is equal to the difference between the two distances 1004, 1006 then k is equal to $(t_2-t_1-T)/c$ where c is the speed of light. Then the mobile unit location 1002 lies on a first hyperbola 1012

$$A(x-a)^2-By^2=C \tag{15}$$

Where $$a=\tfrac{1}{2}(x_2+x_1) \tag{16}$$

$$A=4(x_2-x_1)^2-4k^2$$

$$B=4k^2$$

$$C=2k^2(x_2-x_1)+4k^2h^2-k^4$$

Preferably, the satellite 102 "time stamps" each of the plurality of signals when it is received from the mobile unit 106. In other words, the reception times of each of the signals is recorded. Preferably, each recorded reception time is transmitted to the terrestrial station 108 in a message. The reception times may be transmitted to the terrestrial station 108 in a variety of ways. For example, several reception times may be stored and transmitted in a single message or each reception time may be forwarded in a single message.

In a fourth alternate embodiment, the satellite performs the function of a repeater station by relaying the plurality of signals directly to the terrestrial station 108. In systems utilizing packet switching schemes or other communication techniques that result in variable delays, the terrestrial station compensates for the variable delays using known techniques. The terrestrial station 108 determines the satellite 102 signal reception times based on the times that the plurality of signals are received at the terrestrial station 108 and other communication system parameters. Therefore, the reception times are determined by the terrestrial station 108 in the fourth alternate embodiment and received in a message by the terrestrial station 108 in the third alternate embodiment.

Figure 11:
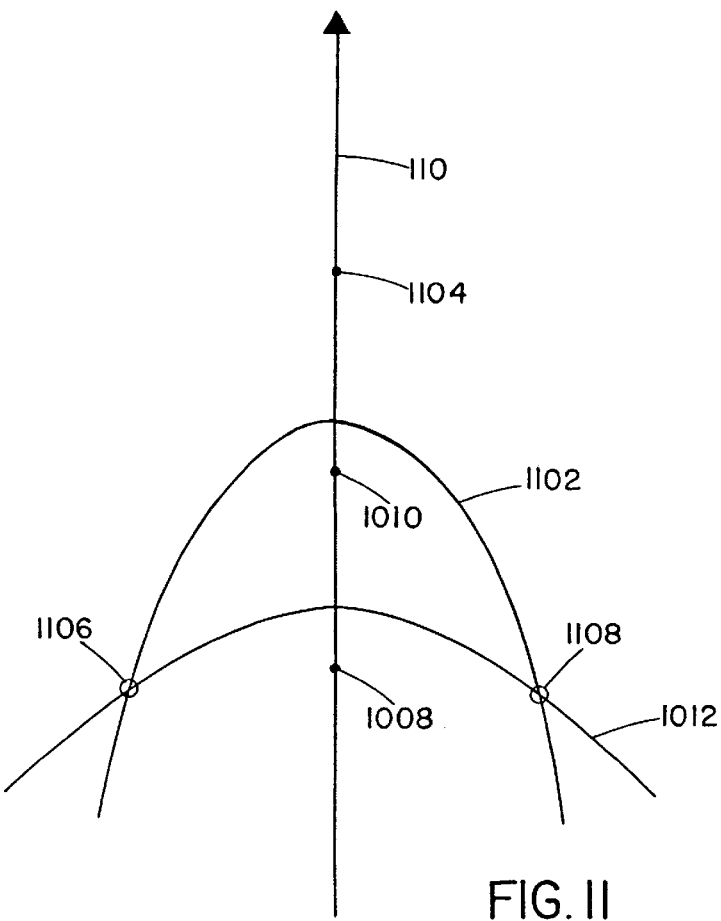
FIG. 11 is a top view of the apparatus receiving the first three signals as it travels above the surface of the earth in accordance with the third and fourth alternate embodiments of the invention.

FIG. 11 is a top view of the apparatus (satellite) 102 traveling above the surface of the earth 104 in accordance with the third alternate embodiment of the invention. The terrestrial station 108 determines the two possible locations 1102, 1104 of the mobile unit 106 using the reception times of the first signal (first reception time) the reception time of the second signal (second reception time) and reception time of the third signal (third reception time). A first instantaneous distance is determined using the first and second reception times. Although similar in many aspects, the instantaneous distances as defined in the preferred embodiment differ from the instantaneous distances as described in regard to the third alternate embodiment. As describer above, the instantaneous distances 308, 310 in the preferred embodiment can be interpredted as a circle defined by a radius that is the length of the instantaneous distance where the circle has a center at the position of the satellite. In the third alternate embdoiment, however, the instantaneous distances define hyperbolas. In other words the geometric curve rpereseting the plurlaioty of posible locations of the mobile unit onm the surface of the earth is a hyperbola rather than a circle. The difference in geometric curves is due to the relationship between the travel time of the signals and the time required for the sateelite to travel a given distance. In the preferred embdoiment, the position of the staellite can be considered to be stationary while the mesaurements are taken to determine an instantaneous distacne. In the third alternate emboidment, however, the motion of the satellite is relevent during the measurement. The satellite can not be considered to be stationary in the third alternate embodiment during the measurements. As a result, the plurality of possible locations of the mobile unit 106 are represented by a hyperbola in the third alternate embodiment and a circle in the preferred embdoiment and are dependent on the terrain of the earth.

By measuring the difference between the first and second reception times and subtracting the predetermined time period, a first time shift is determined. In other words, a reverse Doppler calculation is performed to determine the first instantaneous distance defined by the first hyperbola 1012. Using the first time shift, the terrestrial station 108 determines the first instantaneous distance by applying equation (15) above.

The satellite 102 receives the third signal from the mobile unit 106 at a third reception position 1104. Using the second and third reception times, the terrestrial station 108 determines a second instantaneous distance defined by a second hyperbola 1102. The second instantaneous distance is calculated using the same method as described above except that the second and third reception times are used rather than the first and second receptions times. A reverse Doppler calculation using the second and third reception times yields the second instantaneous distance.

As shown in FIG. 11, the first hyperbola 1012 defines the possible locations of the mobile unit 106 that are the first instantaneous distance from the satellite 102 at the second signal reception time. Similarly, a second hyperbola 1102 defines the possible locations of the mobile unit that are positioned at the second instantaneous distance from the satellite 102 at the third signal reception time. The terrestrial station 108 determines two possible locations 1106, 1108 of the mobile unit 102 based on the intersection of the two hyperbolas 1012, 1102.

The lateral ambiguity in the third and fourth alternate embodiments is resolved using a similar method to the method in the preferred embodiment. In general, the measurement residuals are smaller for the true location of the mobile unit 106 than for the ambiguous location on the opposite side of the satellite ground path 404.

Figure 12:
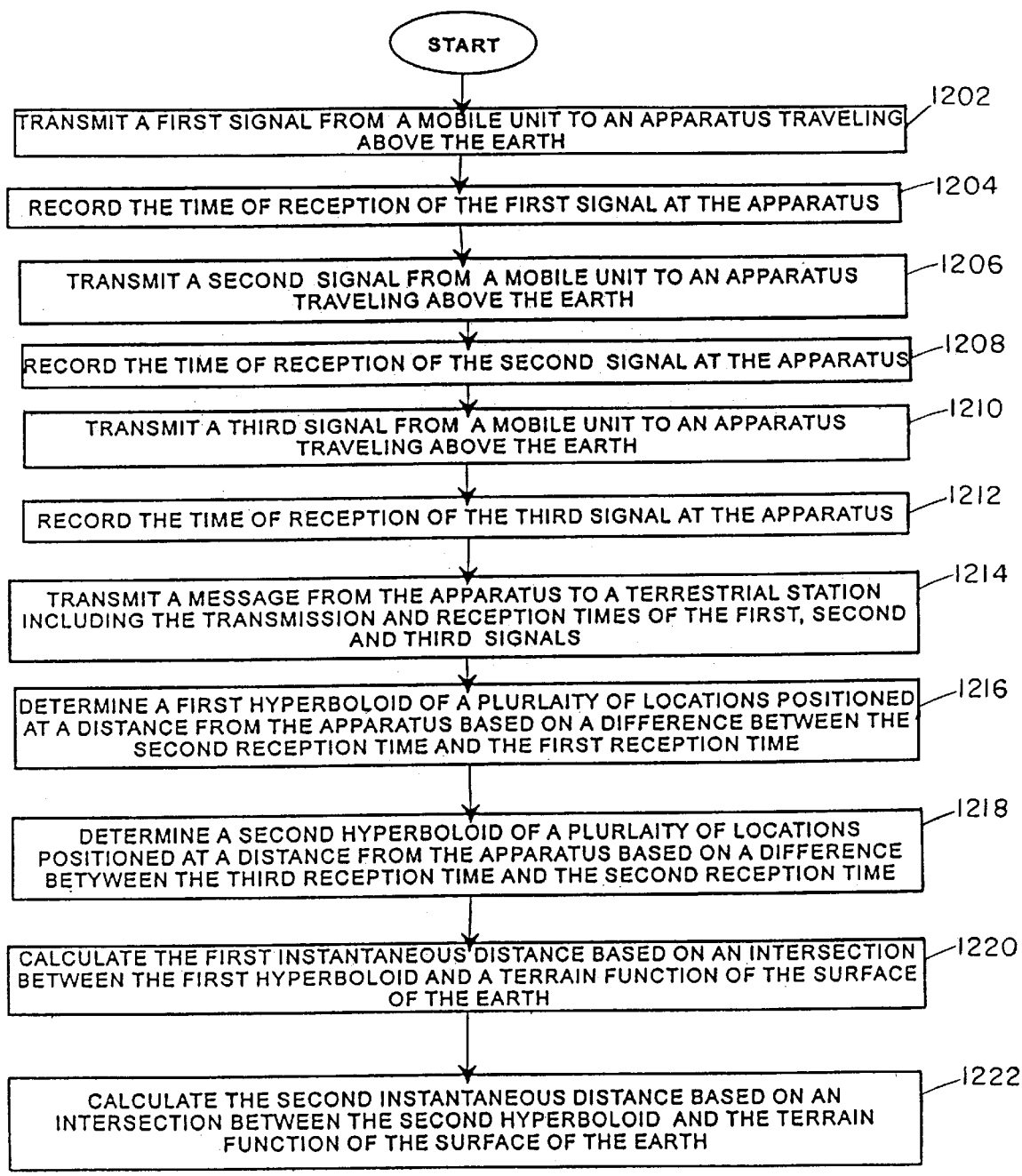
FIG. 12 is a flow chart of a method of determining the first and second instantaneous distances in accordance with the third embodiment of the invention.

FIG. 12 is a flow chart of a method of determining the first instantaneous distance (step 502 in FIG. 5*a*) and the second instantaneous distance (step 504 in FIG. 5*a*) in accordance with the third alternate embodiment of the invention. At step 1202, the mobile unit 106 transmits the first signal to the apparatus (satellite) 102 at a first signal transmission time.

At step 1204, the satellite 102 receives the first signal at the first signal reception time and records the first signal reception time.

At step 1206, the mobile unit 106 transmits a second signal to the satellite 102.

At step 1208, the satellite 102 receives the second signal at the second signal reception time and records the time of reception.

At step 1210, the mobile unit 106 transmits a third signal at the third signal transmission time to the satellite 102.

The satellite 102 records the reception time of the third signal after it receives the signal at the third signal reception time at step 1212.

At step 1214, the satellite 102 transmits a message to the terrestrial station 108 that includes the first signal reception time, the second signal reception time and the third signal reception time.

Using the information in the message in addition to other known data, the terrestrial station 108 determines a first hyperboloid of a plurality of locations positioned relative to the satellite during its travel along the satellite flight path at step 1216. The hyperboloid is based on the difference between the second reception time and the first reception time and the known period between the transmission times of the first and second signals. Those skilled in the art will recognize the similarities between the spheres 320, 322 discussed in regard to the preferred embodiment and the hyperboloids referred to in the third alternate embodiment. As seen above, equation (15) takes into account the intersection of a the plane 402 and the hyperboloid to define the hyperbola 1012. Although the surface of the earth 104 has been approximated as a planar flat surface 402 for demonstrative purposes, those skilled in the art will recognize that the surface of the earth 104 is defined by the terrain function discussed above. Accordingly, at step 1216, the three dimensional hyperboloid is determined and includes all of the possible locations of the mobile unit 106 at the second signal reception time. As will be seen below in regard to step 1220, the intersection between the hyperboloid and the terrain function of the surface of the earth yields a hyperbola 1012 of possible mobile unit locations on the surface of the earth.

At step 1218, the terrestrial station 108 determines the second hyperboloid of a plurality of locations positioned as a distance from the satellite 102 based on the difference between the third signal reception time, the second signal reception time and the period (T) between the second and third transmission times.

The first instantaneous distance is calculated based on the intersection between the first hyperboloid and the terrain function of the surface of the earth 104 at step 1220. Although the surface of the earth 104 may be approximated by a plane 402, the terrain function of the earth 104 more accurately defines the surface. The intersection of the terrain function and the first hyperboloid yields a plurality of possible mobile unit locations (1012) on the surface of the earth. The geometric shape of the plurality of mobile unit locations approaches a hyperbola 1012 as the terrain function more closely defines a plane 402.

At step 1222, the terrestrial station calculates the second instantaneous distance based on the intersection between the second hyperboloid and the terrain function of the surface of the earth 104.

The method of determining the geographical location of a mobile unit in accordance with the third alternate embodiment continues as described in regard to FIGS. 5*a* and 5*c* except that the instantaneous distances are hyperbolic in the third and fourth alternate embodiments and are circular in the preferred embodiment, the first alternate embodiment, and the second alternate embodiment.

Therefore, the location of a mobile unit 106 is determined by sending a plurality of signals from the mobile unit 106 to an apparatus traveling above the surface of the earth. In some embodiments, the signal originates in the apparatus and is retransmitted by the mobile unit after a predetermined retransmission delay. In other embodiments, the signals are generated by the mobile unit 106. Based on the travel times of the signals, several instantaneous distances are determined where in some embodiments the instantaneous distances can be approximated by circles and, in other embodiments, by hyperbolas lying on the surface of the earth. Intersections between the geometric curves representing the instantaneous distances are used to determine two possible locations of the mobile unit 106. The ambiguity is resolved by observing the movement of the mobile unit due to the rotation of the earth.

Although the various embodiments are primarily described using geometric representations, the embodiments are preferably implemented using an algorithm such as the least squares method described above.

The previous descriptions of the preferred embodiment are provided to enable any person skilled in the art to use the present invention. Various modifications to these embodiments will be readily apparent to those skilled in the art, and the generic principles defined herein may be applied to other embodiments without the use of the inventive facility. Therefore, this invention is to be limited only by the following claims, which include all such other embodiments and modifications when viewed in conjunction with the above specification and accompanying drawings.

We claim:

1. A method of determining a geographical location of a mobile unit, the method comprising the steps of:

determining a first instantaneous distance between an apparatus traveling above a surface of Earth and the mobile unit based on a first signal travel time of a first signal;

determining a second instantaneous distance between the apparatus and the mobile unit based on second signal travel time of a second signal;

calculating two possible location regions of the mobile unit based on an intersection of the first instantaneous distance and the second instantaneous distance; and identifying one of the two possible location regions as the location region including the location of the mobile unit by observing a movement of the mobile unit due to a rotation of Earth.

2. A method in accordance with claim 1 wherein the apparatus traveling above the surface of the earth is a satellite.

3. A method in accordance with claim 2 wherein the step of determining the first instantaneous distance comprises the step of multiplying the first signal travel time by the speed of the first signal; and wherein the step of determining the second instantaneous distance comprises the step of multiplying the second signal travel time by the speed of the second signal.

4. A method in accordance with claim 3 wherein the step of determining the first signal travel time comprises the steps of:

transmitting the first signal from the satellite to the mobile unit at a first transmission time;

transmitting the first signal from the mobile unit to the satellite;

receiving the first signal at the satellite at a first signal reception time;

subtracting a known mobile unit signal delay from a first elapsed time between the first transmission time and the first reception time to determine a time equal to twice the first signal travel time.

5. A method in accordance with claim 3 wherein the step of determining the second signal travel time comprises the steps of:

transmitting the second signal from the satellite to the mobile unit at a second transmission time;

transmitting the second signal from the mobile unit to the satellite;

receiving the second signal at the satellite at a second signal reception time;

subtracting a known mobile unit signal delay from a second elapsed time between the second transmission time and the second reception time to determine a time equal to twice the second signal travel time.

6. A method in accordance with claim 3 wherein the step of determining the first signal travel time comprises the steps of:

transmitting the first signal from a ground station to the satellite at a first transmission time;

transmitting the first signal from the satellite to the mobile unit;

transmitting the first signal from the mobile unit to the satellite;

receiving the first signal at the satellite;

transmitting the first signal to the ground station from the satellite;

receiving the first signal at the ground station at a first reception time;

subtracting a known mobile unit signal delay from a first elapsed time between the first transmission time and the first signal reception time;

subtracting a first two way signal travel time between the ground station and the satellite from the first elapsed time to determining the first signal travel time.

7. A method in accordance with claim 3 wherein the step of determining the second signal travel time comprises the steps of:

transmitting the second signal from a ground station to the satellite at a second transmission time;

transmitting the second signal from the satellite to the mobile unit;

transmitting the second signal from the mobile unit to the satellite;

receiving the second signal at the satellite;

transmitting the second signal to the ground station from the satellite;

receiving the second signal at the ground station at a second reception time;

subtracting a known mobile unit signal delay from a second elapsed time between the second transmission time and the second signal reception time;

subtracting a second two way signal travel time between the ground station and the satellite from the second elapsed time to determining the second signal travel time.

8. A method in accordance with claim 3 wherein the step of determining the first signal travel time comprises the steps of:

transmitting a reference signal from the mobile unit to the satellite;

transmitting the first signal from the mobile unit after a first delay time after transmitting the reference signal;

receiving the reference signal at the satellite at a reference signal reception time;

receiving the first signal at the satellite at a first signal reception time; and subtracting the first delay time from a difference between the first signal reception time and the reference signal reception time.

9. A method in accordance with claim 8 wherein the step of determining the second signal travel time comprises the steps of:

transmitting the second signal from the mobile unit after a second delay time after transmitting the first signal;

receiving the second signal at the satellite at a second signal reception time;

subtracting the second delay time from a difference between the second signal reception time and the first signal reception time.

10. A method in accordance with claim 1 further comprising the steps of:

repeating the step of determining the second instantaneous distance to determine a plurality of instantaneous distances;

calculating a plurality of possible locations of the mobile unit based on a plurality of intersections of a last instantaneous distance of the plurality of instantaneous distances and a previous instantaneous distance; and identifying one of the plurality of possible locations as the location of the mobile user.

11. A method in accordance with claim 10 further comprising the step of using the previous instantaneous distance to calculate the last instantaneous distance.

12. A method determining a geographical location of a mobile unit, the method comprising the steps of:

determining a plurality of instantaneous distances between an apparatus traveling above a surface of Earth and the mobile unit based on a plurality of signal travel times of a plurality of signals;

calculating a plurality of possible location pairs of the mobile unit based on an intersection between a last instantaneous distance and a previous instantaneous distance and based on a previous mobile unit location estimate;

identifying a most probable location pair of the possible location pairs as including the location of the mobile unit; and identifying one of two possible locations of the most probable location pair as the location of the mobile unit by observing a movement of the mobile unit due to a rotation of Earth.

13. A method in accordance with claim 12 wherein the apparatus traveling above the surface of the earth is a satellite.

14. An apparatus for determining the geographical location of a mobile unit, the apparatus comprising:

a receiver adapted to receive a first signal at a first reception time and a second signal at a second reception time, the first signal and the second signal transmitted from the mobile unit; wherein the first signal requires a first signal travel time to travel between the apparatus and the mobile unit and wherein the second signal requires a second signal travel time to travel between the apparatus and the mobile unit;

a processor coupled to the receiver, the processor adapted to:

determine a first instantaneous distance between the satellite and the mobile unit based on the first signal travel time;

determine a second instantaneous distance between the satellite and the mobile unit based on the second signal travel time;

calculate two possible location regions of the mobile unit based on an intersection of the first instantaneous distance and the second instantaneous distance; and identify one of the two possible location regions as including the location of the mobile unit by observing a movement of the mobile unit due to a rotation of Earth.

15. An apparatus in accordance with claim 14 further comprising a transmitter coupled to the processor, the transmitter adapted to transmit the first signal at a first transmission time and the second signal at a second transmission time to the mobile unit.

16. A satellite in accordance with claim 15 wherein the processor is adapted to determine the first signal travel time by subtracting a known mobile unit re-transmission delay from an elapsed time between the first transmission time and the first reception time.

17. An apparatus in accordance with claim 16 wherein the processor is adapted to determine the second signal travel time by subtracting a known mobile unit re-transmission delay from an elapsed time between the second transmission time and the second reception time.

18. An apparatus in accordance with claim 17 wherein the receiver is adapted couple to a satellite.

19. An apparatus for determining a geographical location of a mobile unit, the satellite comprising:

a transmitter adapted to transmit a plurality of signals to the mobile unit;

a receiver adapted to receive the plurality of signals re-transmitted from the mobile unit, wherein each of the plurality of signals requires a travel time to travel from the apparatus to the mobile unit resulting in a plurality of travel times; and a processor coupled to the receiver and the transmitter, the processor adapted to:

determine a plurality of instantaneous distances based on the plurality travel times;

calculate two most probable locations of the mobile unit based on a plurality of intersections of the plurality of distances;

identify one of the two most probable locations of the mobile unit as the location of the mobile unit by observing a movement of the mobile unit due to the rotation of Earth.

20. A terrestrial station within a satellite system for determining a geographical location of a mobile unit, the terrestrial station comprising:

a receiver adapted to receive a first signal at a first reception time and a second signal at a second reception time, the first signal and the second signal transmitted from the mobile unit through a satellite; wherein the first signal requires a first signal travel time to travel between the satellite and the mobile unit and wherein the second signal requires a second signal travel time to travel between the satellite and the mobile unit;

a processor coupled to the receiver, the processor adapted to:
 determine a first instantaneous distance between the satellite and the mobile unit based on the first signal travel time;
 determine a second instantaneous distance between the satellite and the mobile unit based on the second signal travel time;
 calculate two possible location regions of the mobile unit based on an intersection of the first instantaneous distance and the second instantaneous distance; and
 identify one of the two possible location regions as including the location of the mobile unit by observing a movement of the mobile unit due to a rotation of Earth.

21. A terrestrial station in accordance with claim 20 further comprising a transmitter coupled to the processor, the transmitter adapted to transmit the first signal at a first transmission time and the second signal at a second transmission time to the mobile unit.

22. A terrestrial station in accordance with claim 21 wherein the processor is adapted to determine the first signal travel time by subtracting a known mobile unit re-transmission delay from an elapsed time between the first transmission time and the first reception time and subtracting a satellite to terrestrial station travel time from the elapsed time.

23. A terrestrial station in accordance with claim 21 wherein the processor is adapted to determine the second signal travel time by subtracting a known mobile unit re-transmission delay from an elapsed time between the second transmission time and the second reception time and subtracting a satellite to terrestrial station travel time from the elapsed time.

24. A method of determining a geographical location of a mobile unit with a single satellite, the method comprising the steps of:

determining a first instantaneous distance between a satellite and the mobile unit based on a difference in time between reception of a first signal and reception of a second signal transmitted from the mobile unit;

determining a second instantaneous distance between the satellite and the mobile unit based on a difference in time between reception of the second signal and reception of a third signal transmitted from the mobile unit;

calculating two possible location regions of the mobile unit based on an intersection of the first instantaneous distance and the second instantaneous distance; and identifying one of the two possible location regions as including the location of the mobile unit based on a difference in time between reception of a fourth signal and the third signal due to a rotation of Earth.

25. A method in accordance with claim 24 wherein the step of determining the first instantaneous distance comprises the step of calculating the first instantaneous distance based on a velocity of the satellite.

26. A method in accordance with claim 24 wherein the step of determining a second instantaneous distance comprises the step of calculating the second distance based on a velocity of the satellite.

27. A method in accordance with claim 24 wherein the step of determining the first instantaneous distance comprises the steps of:

determining a first signal reception time;

determining a second signal reception time;

subtracting the first signal reception time from the second signal reception time to produce a first reception time differential;

subtracting a predetermined time period from the first reception time differential to determine a first time shift, the first signal and the second signal transmitted at times separated by the predetermined time period; and calculating the first instantaneous distance based on the time shift, speed of light and the velocity of the satellite.

28. A method in accordance with claim 27 wherein the step of determining the second instantaneous distance comprises the steps of:

determining a third signal reception time;

determining a fourth signal reception time;

subtracting the third signal reception time from the fourth signal reception time to produce a second reception time differential;

subtracting a second predetermined time period from the second reception time differential to determine a second time shift, the third signal and the fourth signal transmitted at time separated by the second predetermined time period; and calculating the second instantaneous distance based on the time shift, speed of light and the velocity of the satellite.

29. A method in accordance with claim 28, further comprising the step of receiving a plurality of messages from the satellite at the terrestrial station, the messages containing the first reception time, the second reception time, the third reception time and the fourth reception time.

30. A processor coupled within a terrestrial station of a satellite communication system, the processor adapted to performing the steps of:

determining a first instantaneous distance between a satellite and the mobile unit based on a difference in time between reception of a first signal and reception of a second signal transmitted from the mobile unit;

determining a second instantaneous distance between the satellite and the mobile unit based on a difference in time between reception of the second signal and reception of a third signal transmitted from the mobile unit;

calculating two possible location regions of the mobile unit based on an intersection of the first instantaneous distance and the second instantaneous distance; and identifying one of the two possible location regions as including the location of the mobile unit based on a difference in time between reception of a fourth signal and the third signal due to a rotation of Earth.

31. A method determining a geographical location of a mobile unit, the method comprising the steps of:

minimizing residual results of a least squares equation for a plurality of signal travel times between an apparatus traveling above a surface of Earth and the mobile unit to determine two possible location regions of the mobile unit; and identifying one of the two possible location regions as including the location of the mobile unit by observing a convergence of the least squares equation to the location region including the location of the mobile unit due to movement of the mobile unit resulting from a rotation of Earth.

32. A method of determining a geographical location of a mobile unit, the method comprising the steps of:

determining a first geometric equation defining a first plurality of potential instantaneous distances between an apparatus traveling above a surface of Earth and the mobile unit based on a first signal travel time of a first signal;

determining a second geometric equation defining a second plurality of potential instantaneous distance between the apparatus and the mobile unit based on second signal travel time of a second signal;

calculating two possible location regions of the mobile unit based on an intersection of the first geometric equation and the second geometric equation; and identifying one of the two possible location regions as including the location of the mobile unit by observing a movement of the mobile unit due to a rotation of Earth.

33. A method in accordance with claim 32 wherein the apparatus traveling above the surface of the earth is a satellite.

34. A method in accordance with claim 33 wherein the step of determining the first geometric equation comprises the step of multiplying the first signal travel time by the speed of the first signal; and wherein the step of determining the second geometric equation comprises the step of multiplying the second signal travel time by the speed of the second signal.

35. A method in accordance with claim 34 wherein the step of determining the first signal travel time comprises the steps of:

transmitting the first signal from the satellite to the mobile unit at a first transmission time;

transmitting the first signal from the mobile unit to the satellite;

receiving the first signal at the satellite at a first signal reception time;

subtracting a known mobile unit signal delay from a first elapsed time between the first transmission time and the first reception time to determine a time equal to twice the first signal travel time.

36. A method in accordance with claim 34 wherein the step of determining the second signal travel time comprises the steps of:

transmitting the second signal from the satellite to the mobile unit at a second transmission time;

transmitting the second signal from the mobile unit to the satellite;

receiving the second signal at the satellite at a second signal reception time;

subtracting a known mobile unit signal delay from a second elapsed time between the second transmission time and the second reception time to determine a time equal to twice the second signal travel time.

37. A method in accordance with claim 34 wherein the step of determining the first signal travel time comprises the steps of:

transmitting the first signal from a terrestrial station to the satellite at a first transmission time;

transmitting the first signal from the satellite to the mobile unit;

transmitting the first signal from the mobile unit to the satellite;

receiving the first signal at the satellite;

transmitting the first signal to the terrestrial station from the satellite;

receiving the first signal at the terrestrial station at a first reception time;

subtracting a known mobile unit signal delay from a first elapsed time between the first transmission time and the first signal reception time;

subtracting a first two way signal travel time between the ground station and the satellite from the first elapsed time to determining the first signal travel time.

38. A method in accordance with claim 34 wherein the step of determining the second signal travel time comprises the steps of:

transmitting the second signal from a terrestrial station to the satellite at a second transmission time;

transmitting the second signal from the satellite to the mobile unit;

transmitting the second signal from the mobile unit to the satellite;

receiving the second signal at the satellite;

transmitting the second signal to the terrestrial station from the satellite;

receiving the second signal at the terrestrial station at a second reception time;

subtracting a known mobile unit signal delay from a second lapsed time between the second transmission time and the second signal reception time;

subtracting a second two way signal travel time between the terrestrial station and the satellite from the second elapsed time to determining the second signal travel time.

39. A method in accordance with claim 34 wherein the step of determining the first signal travel time comprises the steps of:

transmitting a reference signal from the mobile unit to the satellite;

transmitting the first signal from the mobile unit after a first delay time after transmitting the reference signal;

receiving the reference signal at the satellite at a reference signal reception time;

receiving the first signal at the satellite at a first signal reception time; and subtracting the first delay time from a difference between the first signal reception time and the reference signal reception time.

40. A method in accordance with claim 39 wherein the step of determining the second signal travel time comprises the steps of:

transmitting the second signal from the mobile unit after a second delay time after transmitting the first signal;

receiving the second signal at the satellite at a second signal reception time;

subtracting the second delay time from a difference between the second signal reception time and the first signal reception time.

41. A method in accordance with claim 32 further comprising the steps of:

repeating the step of determining the second geometric equation to determine a plurality of geometric equations, wherein each of the plurality of geometric equations defines a plurality of potential mobile unit locations;

calculating a plurality of possible location regions based on a plurality of intersections of a last geometric equation and a geometric equation; and identifying one of the plurality of possible location regions as including the location of the mobile user.

42. A method in accordance with claim 41 further comprising the step of using the previous geometric equation to calculate the last geometric equation.

43. A satellite communication system comprising:

a mobile unit adapted to transmit a plurality of signals separated by predetermined time intervals;

a satellite orbiting earth and adapted to transmit a plurality of messages conveying reception times of the plurality signals received at the satellite; and a terrestrial station adapted to determine a location of the mobile unit based on time differentials between the reception times; and wherein the terrestrial station determines the location of the mobile unit by:

determining two simultaneous distances between the satellite and the mobile unit based upon the time differential;

determining two possible location regions based on the two simultaneous distances; and identifying one of the two possible location regions as including the location of the mobile unit based on a time difference between the reception times of two signals transmitted by the mobile unit, the time differences resulting from the motion of the mobile unit due to a rotation of Earth.

* * * * *